(12) United States Patent
Wood et al.

(10) Patent No.: US 9,138,957 B2
(45) Date of Patent: Sep. 22, 2015

(54) SLIT HOOK STRIPS AND LAMINATES AND ARTICLES CONTAINING THE SAME

(75) Inventors: Leigh E. Wood, Woodburry, MN (US); Andreas Urban, Cologne (DE); Volker Hauschildt, Hilden (DE)

(73) Assignee: 3M Innovative Properties Company, St. Paul, MN (US)

( * ) Notice: Subject to any disclaimer, the term of this patent is extended or adjusted under 35 U.S.C. 154(b) by 547 days.

(21) Appl. No.: 12/819,808

(22) Filed: Jun. 21, 2010

(65) Prior Publication Data

US 2011/0313389 A1    Dec. 22, 2011

(51) Int. Cl.
| | | |
|---|---|---|
| A44B 18/00 | (2006.01) | |
| A61F 13/56 | (2006.01) | |
| A61F 13/62 | (2006.01) | |
| B32B 3/06 | (2006.01) | |
| B32B 3/26 | (2006.01) | |
| B32B 3/30 | (2006.01) | |
| B32B 5/02 | (2006.01) | |
| B32B 7/12 | (2006.01) | |
| B32B 27/12 | (2006.01) | |
| B32B 27/32 | (2006.01) | |

(52) U.S. Cl.
CPC .............. *B32B 3/06* (2013.01); *A44B 18/0065* (2013.01); *A61F 13/625* (2013.01); *B32B 3/266* (2013.01); *B32B 3/30* (2013.01); *B32B 5/022* (2013.01); *B32B 7/12* (2013.01); *B32B 27/12* (2013.01); *B32B 27/32* (2013.01); *B32B 2250/02* (2013.01); *Y10T 428/24017* (2015.01)

(58) Field of Classification Search
USPC .............. 604/380, 391; 24/306, 452; 264/146
See application file for complete search history.

(56) References Cited

U.S. PATENT DOCUMENTS

| | | |
|---|---|---|
| 3,191,255 A | 6/1965 | Nealis |
| 3,192,589 A | 7/1965 | Pearson |
| 3,717,908 A | 2/1973 | Perina |

(Continued)

FOREIGN PATENT DOCUMENTS

| | | |
|---|---|---|
| CN | 1030011 | 1/1989 |
| DE | 102006038334 | 2/2008 |

(Continued)

OTHER PUBLICATIONS

U.S. Application entitled, "Method of Making a Mechanical Fastening Strip and Reticulated Mechanical Fastening Strip Therefrom", filed Feb. 16, 2011, having U.S. Appl. No. 13/028,912.

(Continued)

*Primary Examiner* — Lynne Anderson
*Assistant Examiner* — Peter S Vasat

(57) ABSTRACT

A hook strip is provided having a backing with a first surface and a length in a first direction; multiple rows of hook elements aligned in the first direction and projecting from the first surface of the backing; and slits in the backing between at least some pairs of adjacent rows of the hook elements. The slits may be interrupted by a bridging region of the backing, or the slits may be partial slits that penetrate the thickness of the backing in a range from 40 to 90 percent. A fastening laminate that includes a carrier and the hook strip described above joined to the carrier is also provided. In some embodiments, the fastening laminate includes slits that form separate, abutting portions of the backing on the carrier. An absorbent article containing the hook strip and a method of making the hook strip are also disclosed.

19 Claims, 10 Drawing Sheets

(56) References Cited

U.S. PATENT DOCUMENTS

| | | | |
|---|---|---|---|
| 3,770,359 A | 11/1973 | Hamano | |
| 4,001,366 A | 1/1977 | Brumlik | |
| 4,568,344 A | 2/1986 | Suzuki | |
| 4,585,450 A | 4/1986 | Rosch | |
| 4,894,060 A | 1/1990 | Nestegard | |
| 5,077,870 A | 1/1992 | Melbye | |
| 5,256,231 A | 10/1993 | Gorman | |
| 5,260,015 A | 11/1993 | Kennedy | |
| 5,300,058 A | 4/1994 | Goulait | |
| 5,318,555 A | 6/1994 | Siebers | |
| 5,605,735 A | 2/1997 | Zehner | |
| 5,607,635 A | 3/1997 | Melbye | |
| 5,660,666 A | 8/1997 | Dilnik | |
| 5,679,302 A | 10/1997 | Miller | |
| 5,692,271 A | 12/1997 | Provost | |
| 5,781,969 A | 7/1998 | Akeno et al. | |
| 5,800,845 A | 9/1998 | Akeno et al. | |
| 5,845,375 A | 12/1998 | Miller | |
| 5,868,987 A | 2/1999 | Kampfer | |
| 5,879,604 A | 3/1999 | Melbye | |
| 5,913,482 A | 6/1999 | Akeno | |
| 5,930,875 A | 8/1999 | Schreiner | |
| 5,945,131 A | 8/1999 | Harvey | |
| 5,957,908 A | 9/1999 | Kline | |
| 5,961,761 A | 10/1999 | Heindel et al. | |
| 5,997,522 A | 12/1999 | Provost | |
| 6,000,106 A | 12/1999 | Kampfer | |
| 6,030,373 A | 2/2000 | VanGompel | |
| 6,039,911 A | 3/2000 | Miller | |
| 6,054,091 A | 4/2000 | Miller | |
| 6,075,179 A | 6/2000 | McCormack | |
| 6,132,660 A | 10/2000 | Kampfer | |
| 6,146,369 A | 11/2000 | Hartman | |
| 6,162,040 A | 12/2000 | Clune | |
| 6,190,758 B1 | 2/2001 | Stopper | |
| 6,406,468 B1 | 6/2002 | Dilnik | |
| 6,419,667 B1 | 7/2002 | Avalon | |
| 6,463,633 B1 | 10/2002 | Sangani | |
| 6,489,003 B1 | 12/2002 | Levitt | |
| 6,540,497 B1 | 4/2003 | Fuda et al. | |
| 6,544,245 B2 | 4/2003 | Neeb | |
| 6,546,604 B2 | 4/2003 | Galkiewicz et al. | |
| 6,558,602 B1 | 5/2003 | Melbye | |
| 6,575,953 B2 | 6/2003 | Olson | |
| 6,588,073 B1 | 7/2003 | Zoromski | |
| 6,592,800 B1 | 7/2003 | Levitt et al. | |
| 6,627,133 B1 | 9/2003 | Tuma | |
| 6,635,212 B1 | 10/2003 | Melbye | |
| 6,708,378 B2 | 3/2004 | Parellada et al. | |
| 6,899,841 B2 * | 5/2005 | Buzzell et al. | 264/167 |
| 6,994,698 B2 | 2/2006 | Leak | |
| 7,032,278 B2 | 4/2006 | Kurtz, Jr. | |
| 7,048,527 B2 | 5/2006 | Bay et al. | |
| 7,048,818 B2 | 5/2006 | Krantz | |
| 7,052,636 B2 | 5/2006 | Ausen et al. | |
| 7,125,400 B2 | 10/2006 | Igaue | |
| 7,219,403 B2 | 5/2007 | Miyamoto | |
| 7,223,314 B2 | 5/2007 | Provost | |
| 7,241,483 B2 | 7/2007 | Ausen | |
| 7,361,246 B2 | 4/2008 | Chang | |
| 7,371,302 B2 | 5/2008 | Miyamoto | |
| 7,373,698 B2 | 5/2008 | Erdman | |
| 7,407,496 B2 | 8/2008 | Petersen | |
| 7,444,722 B2 | 11/2008 | McDaniel | |
| 7,578,813 B2 | 8/2009 | Mitsui | |
| 7,658,813 B2 | 2/2010 | Petersen | |
| 7,670,522 B2 | 3/2010 | Ausen | |
| 7,727,440 B2 | 6/2010 | Armela et al. | |
| 7,785,095 B2 | 8/2010 | Clune et al. | |
| 8,020,262 B2 | 9/2011 | Oertel | |
| 2002/0016581 A1 | 2/2002 | Kline | |
| 2003/0008106 A1 | 1/2003 | Guenther | |
| 2003/0034583 A1* | 2/2003 | Provost | 264/146 |
| 2003/0049439 A1 | 3/2003 | Johansson et al. | |
| 2003/0085492 A1 | 5/2003 | Schulte | |
| 2003/0130644 A1* | 7/2003 | Baker | 604/389 |
| 2003/0145440 A1 | 8/2003 | Ausen | |
| 2003/0182776 A1 | 10/2003 | Ausen | |
| 2004/0068848 A1 | 4/2004 | Ausen | |
| 2004/0111844 A1 | 6/2004 | Ausen | |
| 2004/0121694 A1 | 6/2004 | Shepard | |
| 2004/0147890 A1 | 7/2004 | Nakahata | |
| 2004/0261232 A1 | 12/2004 | Kurtz, Jr. | |
| 2004/0261233 A1 | 12/2004 | Kingsford | |
| 2005/0079321 A1 | 4/2005 | Tuman et al. | |
| 2005/0283954 A1 | 12/2005 | Erdman et al. | |
| 2006/0293635 A1 | 12/2006 | Petersen | |
| 2007/0035060 A1 | 2/2007 | Harvey | |
| 2007/0039142 A1 | 2/2007 | Petersen | |
| 2007/0134489 A1 | 6/2007 | Neugebauer | |
| 2007/0143972 A1 | 6/2007 | Kline et al. | |
| 2008/0052881 A1 | 3/2008 | Oertel | |
| 2008/0281286 A1 | 11/2008 | Petersen | |
| 2009/0217492 A1 | 9/2009 | Gallant | |
| 2009/0311465 A1* | 12/2009 | De Jong | 428/101 |
| 2011/0147475 A1 | 6/2011 | Biegler | |
| 2011/0151171 A1 | 6/2011 | Biegler | |

FOREIGN PATENT DOCUMENTS

| | | |
|---|---|---|
| EP | 0191355 | 8/1986 |
| EP | 0341993 | 11/1989 |
| EP | 0539504 | 5/1993 |
| EP | 0755665 | 1/1997 |
| EP | 0941730 | 9/1999 |
| EP | 1066008 | 1/2001 |
| EP | 1641417 | 4/2006 |
| EP | 2179671 | 4/2010 |
| JP | 01-250201 | 10/1989 |
| JP | 02-017006 | 1/1990 |
| JP | 09-313536 | 12/1997 |
| JP | 3901315 | 4/2007 |
| JP | 2010-29532 | 2/2010 |
| WO | WO 94/02091 | 2/1994 |
| WO | WO 96/03101 | 2/1996 |
| WO | WO 96/10481 | 4/1996 |
| WO | WO 96/19174 | 6/1996 |
| WO | WO 00-15069 | 3/2000 |
| WO | WO 00/50229 | 8/2000 |
| WO | WO 01/68019 | 9/2001 |
| WO | 2005/016211 | 2/2005 |
| WO | WO 2009/123253 | 10/2009 |

OTHER PUBLICATIONS

U.S. Application entitled, "Method of Making a Structured Surface and Article Therefrom", filed Jun. 15, 2011, having U.S. Appl. No. 61/497,252.

U.S. Application entitled, "Reticulated Mechanical Fastening Patch and Method of Making the Same", filed Jun. 21, 2011, having U.S. Appl. No. 61/499,470.

International Search Reoort from International Application No. PCT/US2011/041019, dated Mar. 19, 2012.

Supplementary European Search Report for Application No. EP 11 79 8693.5, Mar. 12, 2014, 4 pages.

Search Report from CN Application 201180030912.8, filed Jun. 21, 2011, dated Nov. 24, 2014.

US 5,389,416, 02/1995, Mody (withdrawn)

* cited by examiner

SLIT HOOK STRIPS AND LAMINATES AND ARTICLES CONTAINING THE SAME

BACKGROUND

Hook and loop fastening systems, where the hook member typically includes a plurality of closely spaced upstanding projections with loop-engaging heads, and the loop member typically includes a plurality of woven, nonwoven, or knitted loops, are useful for providing releasable attachment in numerous applications. For example, hook and loop fastening systems are widely used in wearable disposable absorbent articles to fasten such articles around the body of a person. In typical configurations, a hook strip or patch on a fastening tab attached to the rear waist portion of a diaper or incontinence garment, for example, can fasten to a landing zone of loop material on the front waist region, or the hook strip or patch can fasten to the backsheet (e.g., nonwoven backsheet) of the diaper or incontinence garment in the front waist region.

Hook and loop fastening systems can include at least two engagement strength characteristics: peel strength and shear strength. Peel strength corresponds to the force required to disengage the fastening members from one another by peeling one fastening member upward and away from the other fastening member. Shear strength corresponds to the force required to disengage the fastening members from one another by pulling at least one of the fastening members away from the other in a plane that is parallel to the fastening members. Typically, the engagement strength of the fastening members is higher in shear than in peel.

When a user wishes to separate the hook and loop fastening members (e.g., on an absorbent article such as a diaper), typically the user peels the fastening members apart. The ease with which the fastening members can peel apart affects the user's perception of the reliability of the attachment between the fastening members. For example, when a caregiver removes a diaper from a baby, if the hook strip feels like it peels too easily from the loop landing zone or backsheet of the diaper, the caregiver may question how well the fastening members can keep the diaper closed when it is in use. And in some instances low peel strength can result in inadvertent separation of the fastening members while the diaper is being worn.

Despite the progress in hook and loop fastening technology, an enhancement in the reliability of the attachment between the fastening members, whether actual or perceived, would be desirable.

SUMMARY

The present disclosure provides a hook strip that comprises slits in a backing between rows of hook elements. The slits may be interrupted slits that are interrupted by bridging regions of the backing, partial slits that extend only partially through the backing, or a combination thereof. The present disclosure also provides a fastening laminate and absorbent article that comprise either the hook strip described above or a hook strip with slits in the backing between rows of hook elements that form separate, abutting strips of the backing on a carrier. The hook strip disclosed herein in any of these embodiments typically has remarkably high peel strength in comparison to a comparative hook strip that is not slit.

In one aspect, the present disclosure provides a hook strip comprising a backing having a first surface and a length in a machine direction; multiple rows of hook elements aligned in the machine direction and projecting from the first surface of the backing; and an interrupted slit cut through the backing between at least one pair of adjacent rows of the hook elements, wherein the interrupted slit extends in the machine direction and is interrupted by at least one intact bridging region of the backing; wherein any intact bridging regions of the backing between one pair of adjacent rows of hook elements have a combined length in the machine direction of up to fifty percent of the length of the backing in the machine direction. In some embodiments, the first surface of the backing is provided with partial-depth cuts in at least some of the bridging regions, wherein the cuts are collinear with the interrupted slits but do not extend through the backing. In some embodiments, there are interrupted slits cut through the backing between at least three pairs of adjacent rows of the hook elements, and the number of rows of hook elements between at least some of the interrupted slits varies.

In another aspect, the present disclosure provides hook strip comprising a backing having a first surface and a length in a first direction; multiple rows of hook elements aligned in the first direction and projecting from the first surface of the backing; an interrupted slit cut through the backing between at least one pair of adjacent rows of the hook elements, wherein the interrupted slit extends in the first direction and is interrupted by at least one intact bridging region of the backing; and a partial-depth cut in the at least one intact bridging region, wherein the partial-depth cut is collinear with the interrupted slit but does not extend through the backing. In some embodiments, there are interrupted slits cut through the backing between at least three pairs of adjacent rows of the hook elements, and the number of rows of hook elements between at least some of the interrupted slits varies.

In another aspect, the present disclosure provides a hook strip comprising a backing having a first surface and a length in a first direction; multiple rows of hook elements aligned in the first direction and projecting from the first surface of the backing; and interrupted slits cut through the backing between at least three pairs of adjacent rows of the hook elements, wherein each of the interrupted slits extends in the first direction and is interrupted by an intact bridging region of the backing; wherein the number of rows of hook elements between at least some of the interrupted slits varies.

In some embodiments of the foregoing aspects, there are interrupted slits cut through the backing between at least two pairs of adjacent rows of the hook elements, wherein for any two adjacent interrupted slits, the bridging regions are staggered in a second direction perpendicular to the first direction. In some embodiments, there are up to seven rows of hook elements between any two adjacent interrupted slits cut through the backing. In some embodiments, any bridging regions of the backing between a pair of adjacent rows of hook elements have a combined length in the machine or first direction of up to fifteen percent of the length of the backing in the machine or first direction.

In another aspect, the present disclosure provides a hook strip comprising a backing having a first surface, a thickness, and a length in a first direction; multiple rows of hook elements aligned in the first direction and projecting from the first surface of the backing; and a partial slit cut into the first surface of the backing between at least one pair of adjacent rows of the hook elements, wherein the partial slit extends in the first direction and penetrates the thickness of the backing in a range from 40 to 90 percent. In some embodiment, there are partial slits cut into the first surface of the backing between at least three pairs of the hook elements, wherein the number of rows of hook elements between at least some of the partial slits varies. In another aspect, the present disclosure provides a hook strip comprising a backing having a first surface, a thickness, and a length in a first direction; multiple rows of hook elements aligned in the first direction and projecting from the first surface of the backing; and partial slits cut into the first surface of the backing between at least three pairs of adjacent rows of the hook elements, wherein each of the partial slits penetrates only partially through the thickness of the backing, and wherein the number of rows of hook elements between at least some of the partial slits varies. In some embodiments, the backing can be bent at least 90 degrees at each partial slit at least five times without rupturing. In some embodiments, at least one of the partial slits is interrupted by at least one bridging region of the backing that is not slit. In other embodiments, at least one of the partial slits penetrates into the thickness of the backing to a different extent in different regions along the length of the backing. In some embodiments, there are at most seven rows of hook elements between any two adjacent partial slits.

In some embodiments of any of the foregoing aspects, the backing is not joined to a carrier. In some embodiments, the multiple rows of hook elements are evenly spaced. In some embodiments when the hook strip is engaged with a loop material, a peel curve defined by load versus peel extension generated upon peeling the hook strip from the loop material has a greater area under the curve than a comparative peel curve generated upon peeling a comparative hook strip from an equivalent loop material, wherein the comparative hook strip is the same as the hook strip except that the comparative hook strip has no interrupted slits or partial slits. In some embodiments when the hook strip is engaged with a loop material, a peel curve defined by load versus peel extension generated upon peeling the hook strip from the loop material has an area under the peel curve at one-half of the peel extension is at least 30 percent of a total area under the peel curve. In some embodiments, when the hook strip is engaged with a loop material and then peeled from the loop material at a peel angle of 135 to 180 degrees, a peel angle of an individual row of hook elements at a distance from a peel front is greater than a peel angle of an individual row of hook elements in a comparative hook strip at the distance from the peel front when the comparative hook strip is peeled from an equivalent loop material, wherein the comparative hook strip is the same as the hook strip except that the comparative hook strip has no interrupted or partial slits.

In another aspect, the present disclosure provides a fastening laminate comprising a carrier and a hook strip according to any of the foregoing aspects or embodiments, wherein the backing has a second surface opposite the first surface, and wherein the second surface of the backing is joined to a portion of the carrier.

In another aspect, the present disclosure provides a fastening laminate comprising a carrier; a backing having a first surface, a second surface opposite the first surface, a thickness, a length in a first direction, a top edge and a bottom edge, wherein the second surface of the backing is joined to a portion of the carrier; multiple evenly spaced rows of hook elements aligned in the first direction and projecting from the first surface of the backing; and slits cut through the backing between at least some pairs of adjacent rows of the hook elements, wherein each of the slits extends in the first direction from the top edge to the bottom edge of the backing to form separate, abutting strips of the backing on the carrier; wherein at least the portion of the carrier to which the second surface of the backing is joined has up to a ten percent elongation in a second direction perpendicular to the first direction.

In another aspect, the present disclosure provides a fastening laminate comprising a carrier; a backing having a first surface, a second surface opposite the first surface, a thickness, a length in a first direction, a top edge and a bottom edge, wherein the second surface of the backing is joined to a portion of the carrier; multiple rows of hook elements aligned in the first direction and projecting from the first surface of the backing; and slits cut into the backing between at least three pairs of adjacent rows of the hook elements, wherein each of the slits extends in the first direction and forms abutting portions of the backing on either side of the slit, and wherein the number of rows of hook elements between at least some of the slits varies; wherein at least the portion of carrier to which the second face of the backing is joined has up to a ten percent elongation in a second direction perpendicular to the first direction. In some embodiments, each of the slits is cut through the thickness of the backing and extends from the top edge to the bottom edge of the backing to form separate, abutting strips of the backing on the carrier. In other embodiments, each of the slits is a partial slit cut into the first face of the backing that penetrates only partially through the thickness of the backing. In other embodiments, each of the slits is an interrupted slit that is cut through the backing and interrupted by a bridging region of the backing, wherein the bridging region of the backing is collinear with the interrupted slit but is not cut or penetrates only a portion of the thickness of the backing. In some embodiments, the fastening laminate has a proximal end (e.g., for permanent attachment to an absorbent article) and a distal end (e.g., for the user to grasp), and the number of rows of hook elements between the slits increases from the distal end to the proximal end.

In some embodiments of the foregoing aspects of fastening laminates, the carrier is fibrous, and the second surface of the backing is surface-bonded to the carrier. In some embodiments, when the fastening laminate is engaged with a loop material, a peel curve defined by load versus peel extension generated upon peeling the hook strip from the loop material has a greater area under the curve than a comparative peel curve generated upon peeling a comparative laminate from an equivalent loop material, wherein the comparative laminate is the same as the fastening laminate except that the comparative laminate has no slits. In some embodiments when the fastening laminate is engaged with a loop material, a peel curve defined by load versus peel extension generated upon peeling the fastening laminate from the loop material has an area under the peel curve at one-half of the peel extension is at least 30 percent of a total area under the peel curve. In some embodiments, when the fastening laminate is engaged with a loop material and then peeled from the loop material at a peel angle of 135 to 180 degrees, a peel angle of an individual row of hook elements at a distance from a peel front is greater than a peel angle of an individual row of hook elements in a comparative hook strip at the distance from the peel front when the comparative hook strip is peeled from an equivalent loop material, wherein the comparative hook strip is the same as the hook strip except that the comparative hook strip has no slits. In some embodiments, there are at most seven rows of hook elements between any two adjacent slits.

In another aspect, the present disclosure provides an absorbent article having at least a front waist region, a rear waist region, and a longitudinal center line bisecting the front waist region and the rear waist region, wherein at least one of the front waist region or the rear waist region comprises a fastening laminate according to any of the foregoing aspects or embodiments, and wherein the machine direction or first direction of the hook strip is aligned with the longitudinal center line.

In another aspect, the present disclosure provides a method of making multiple hook strips, the method comprising forming a continuous web having a backing and multiple rows of hook elements aligned in rows in a machine direction and projecting from a first surface of the backing; cutting incomplete slits in the machine direction in the backing between at least some pairs of adjacent rows of the hook elements, wherein the incomplete slits do not sever the backing; and cutting complete slits in the machine direction through the backing, wherein the complete slits sever the backing; wherein the complete and incomplete slits are positioned such that each of the multiple hook strips has at least one incomplete slit cut into the backing in the machine direction. In some embodiments, the incomplete slits are interrupted slits that are interrupted an intact bridging regions of the backing. In some of these embodiments, for any two adjacent interrupted slits, the bridging regions are staggered in a second direction perpendicular to the first direction. In some embodiments, any bridging regions between a pair of adjacent rows have a combined length in the machine direction of up to fifty percent of the length of the continuous web in the first direction. In some embodiments, the incomplete slits are partial slits that penetrate the thickness of the backing in a range from 40 to 90 percent. In some embodiments, the continuous web is not joined to a carrier web. In other embodiments, the method further comprises joining the continuous web to a carrier web. In some of these embodiments, the carrier web is a fibrous web, and the laminating comprises impinging heated fluid onto a first surface of the fibrous web while it is moving; impinging heated fluid onto the second surface of the backing while the continuous web is moving, wherein the second surface is opposite the first surface of the backing; and contacting the first surface of the fibrous web with the second surface of the backing so that the first surface of the fibrous web is melt-bonded to the second surface of the backing. In some embodiments, the method further comprises cutting at least one of the multiple strips at an angle to the machine direction to provide an individual hook strip. In some embodiments, the method further comprises providing an absorbent article having at least a front waist region and a back waist region; and positioning the individual hook strip on at least one of the front waist region or the back waist region of the absorbent article. In some embodiments, the method further comprises stretching the continuous web in at least one direction to provide stretch-induced molecular orientation. In some embodiments, when the hook strip is engaged with a loop material, a peel curve defined by load versus peel extension generated upon peeling the hook strip from the loop material has a greater area under the curve than a comparative peel curve generated upon peeling a comparative hook strip from an equivalent loop material, wherein the comparative hook strip is the same as the hook strip except that the comparative hook strip has no incomplete slits. In some embodiments when the hook strip is engaged with a loop material, a peel curve defined by load versus peel extension generated upon peeling the hook strip from the loop material has an area under the peel curve at one-half of the peel extension is at least 30 percent of a total area under the peel curve. In some embodiments, when the hook strip is engaged with a loop material and then peeled from the loop material at a peel angle of 135 to 180 degrees, a peel angle of an individual row of hook elements at a distance from a peel front is greater than a peel angle of an individual row of hook elements in a comparative hook strip at the distance from the peel front when the comparative hook strip is peeled from an equivalent loop material, wherein the comparative hook strip is the same as the hook strip except that the comparative hook strip has no incomplete slits. In some embodiments, there are at most seven rows of hook elements between any two adjacent incomplete slits in the backing.

In some embodiments of the foregoing aspects and embodiments, the hook elements have loop-engaging overhangs. In some of these embodiments, at least a portion of each loop-engaging overhang extends at a nonzero angle to first direction (in some embodiments, the machine direction). In some embodiments, the backing exhibits stretch-induced molecular orientation in at least one direction (in some embodiments, the machine direction or first direction). In other embodiments, backing is not stretched beyond what stretching may occur in the machine direction during extrusion.

In this application, terms such as "a", "an" and "the" are not intended to refer to only a singular entity, but include the general class of which a specific example may be used for illustration. The terms "a", "an", and "the" are used interchangeably with the term "at least one". The phrases "at least one of" and "comprises at least one of" followed by a list refers to any one of the items in the list and any combination of two or more items in the list. All numerical ranges are inclusive of their endpoints and non-integral values between the endpoints unless otherwise stated.

The terms "first" and "second" are used in this disclosure. It will be understood that, unless otherwise noted, those terms are used in their relative sense only. In particular, in some embodiments certain components may be present in interchangeable and/or identical multiples (e.g., pairs). For these components, the designation of "first" and "second" may be applied to the components merely as a matter of convenience in the description of one or more of the embodiments.

The term "row" refers to hook elements lined up in a particular direction. The row or line of hook elements may be substantially straight. When an interrupted slit, a partial slit, a slit, a slit that forms separate, abutting regions of the backing, or an incomplete slit is cut between adjacent rows of hook elements, it means that the particular slit does not cross over a row of hook elements.

When it is said that a slit (e.g., interrupted slit, a partial slit, a slit that forms separate, abutting regions of the backing, or an incomplete slit) "extends" in a particular direction, it is meant that the slit is arranged or aligned in that direction or at least predominantly in that direction. The slit may be linear. As used herein a "linear" slit (e.g., interrupted slit, a partial slit, a slit that forms separate, abutting regions of the backing, or an incomplete slit) can be defined by two points in a line between two rows of hook elements. The slit may also be substantially linear, which means that the slit can have a slight curvature or slight oscillation. Some oscillation or curvature may result, for example, from the process of slitting a continuous web as would be understood by a person skilled in the art. Any oscillation or curvature is such that the slit generally does not have a portion that crosses over a row of hook elements. The slit may also have a wavy or sawtooth pattern with a small amplitude such that the pattern generally does not cross over a row of hook elements.

A slit that is cut "through" the backing means that the slit cuts through the entire thickness of the backing.

The term "multiple" refers to more than one. In some embodiments, a hook strip, fastening, laminate, absorbent article, or method according to the present disclosure having multiple rows of hook elements comprises at least 2, 4, 5, 6, 7, 8, 9, 10, 12, 14, 15, or 16 rows of hook elements.

The term "hook element" as used herein refers to male fastening elements that include stems with or without loop-engaging heads that have an overhang. The term "loop-engaging" as used herein relates to the ability of a hook element to be mechanically attached to a loop material. Generally, hook elements with loop-engaging heads have a head shape that is different from the shape of the stem. For example, the hook element may be in the shape of a mushroom (e.g., with a circular or oval head enlarged with respect to the stem), a hook, a palm-tree, a nail, a T, or a J. The loop-engageability of hook elements may be determined and defined by using standard woven, nonwoven, or knit materials. A region of hook elements with loop-engaging heads generally will provide, in combination with a loop material, at least one of a higher peel strength, higher dynamic shear strength, or higher dynamic friction than a region of stems without loop-engaging heads. Hook elements that have "loop-engaging overhangs" or "loop-engaging heads" do not include ribs that are precursors to hook elements (e.g., elongate ribs that are profile extruded and subsequently cut to form hook elements upon stretching in the direction of the ribs). Such ribs would not be able to engage loops before they are cut and stretched. Typically, hook elements that have loop-engaging heads have a maximum thickness dimension of up to about 1 (in some embodiments, 0.9, 0.8, 0.7, 0.6, 0.5, or 0.45) millimeter.

The term "machine direction" (MD) as used above and below denotes the direction of a running, continuous web of the backing during the manufacturing of the hook strip. When a hook strip is cut into smaller portions from a continuous web, the machine direction corresponds to the length "L" of the hook strip. As used herein, the terms machine direction and longitudinal direction are typically used interchangeably. The term "cross-direction" (CD) as used above and below denotes the direction which is essentially perpendicular to the machine direction. When a hook strip is cut into smaller portions from a continuous web, the cross direction corresponds to the width "W" of the hook strip.

For some embodiments, slits (e.g., partial slits) are said to penetrate the thickness of the backing in a certain percent range. The percent penetration may be calculated as depth of the slit divided by the thickness of the backing, with the quotient multiplied by 100.

The term "nonwoven" when referring to a sheet or web means having a structure of individual fibers or threads which are interlaid, but not in an identifiable manner as in a knitted fabric. Nonwoven fabrics or webs can be formed from various processes such as meltblowing processes, spunbonding processes, spunlacing processes, and bonded carded web processes.

The term "elastic" refers to any material that exhibits recovery from stretching or deformation. Likewise, the term "nonelastic" refers to any material that does not exhibit recovery from stretching or deformation.

"Elongation" in terms of percent refers to {(the extended length–the initial length)/the initial length} multiplied by 100.

The term "surface-bonded" when referring to the bonding of fibrous materials means that parts of fiber surfaces of at least portions of fibers are melt-bonded to the second surface of the backing, in such a manner as to substantially preserve the original (pre-bonded) shape of the second surface of the backing, and to substantially preserve at least some portions of the second surface of the backing in an exposed condition, in the surface-bonded area. Quantitatively, surface-bonded fibers may be distinguished from embedded fibers in that at least about 65% of the surface area of the surface-bonded fiber is visible above the second surface of the backing in the bonded portion of the fiber. Inspection from more than one angle may be necessary to visualize the entirety of the surface area of the fiber.

The term "loft-retaining bond" when referring to the bonding of fibrous materials means a bonded fibrous material comprises a loft that is at least 80% of the loft exhibited by the material prior to, or in the absence of, the bonding process. The loft of a fibrous material as used herein is the ratio of the total volume occupied by the web (including fibers as well as interstitial spaces of the material that are not occupied by fibers) to the volume occupied by the material of the fibers alone. If only a portion of a fibrous web has the second surface of the backing bonded thereto, the retained loft can be easily ascertained by comparing the loft of the fibrous web in the bonded area to that of the web in an unbonded area. It may be convenient in some circumstances to compare the loft of the bonded web to that of a sample of the same web before being bonded, for example, if the entirety of fibrous web has the second surface of the backing bonded thereto.

The above summary of the present disclosure is not intended to describe each disclosed embodiment or every implementation of the present disclosure. The description that follows more particularly exemplifies illustrative embodiments. It is to be understood, therefore, that the drawings and following description are for illustration purposes only and should not be read in a manner that would unduly limit the scope of this disclosure.

BRIEF DESCRIPTION OF THE DRAWINGS

The disclosure may be more completely understood in consideration of the following detailed description of various embodiments of the disclosure in connection with the accompanying drawings, in which.

DETAILED DESCRIPTION

Figure 1:
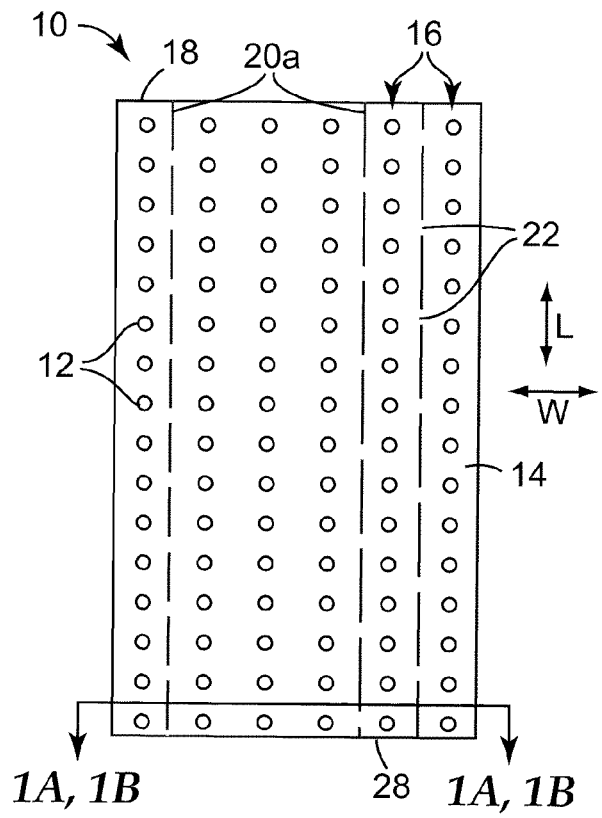
FIG. 1 is a top view of an exemplary hook strip according to the present disclosure.

Reference will now be made in detail to embodiments of the disclosure, one or more examples of which are illustrated in the drawings. Features illustrated or described as part of one embodiment can be used with other embodiments to yield still a third embodiment. It is intended that the present disclosure include these and other modifications and variations.

FIG. 1 illustrates a hook strip 10 according to some embodiments of the present disclosure. Hook strip 10 has a backing 14 with multiple rows 16 of hook elements 12 projecting from a first surface of the backing 14. The first surface of the backing is the surface that is visible in FIG. 1. The first surface can also be called the first major surface in any of the embodiments disclosed herein. The multiple rows 16 are aligned in at least a first direction; in the illustrated embodiment, the rows 16 of hook elements 12 are aligned in the longitudinal direction L. Interrupted slits 20a are cut into the backing between some pairs of adjacent rows 16 of hook elements 12. It should be understood generally that when slits are cut between at least some pairs of adjacent rows 16, there are at least two slits in the backing 14. The interrupted slits 20a are linear in the same direction "L" as the multiple rows 16 and extend from the top edge 18 to the bottom edge 28 of the backing 14. The interrupted slits are interrupted by intact bridging regions 22 of the backing 14. The bridging regions 22 are regions where the backing is not cut through, and they are collinear with interrupted slit 20a. In the illustrated embodiment, the interrupted slits 20a are not evenly spaced among the rows of hook elements 12. There are three rows 16 of hook elements 12 between some adjacent interrupted slits 20a, and one row 16 of hook elements 12 between other adjacent interrupted slits 20a. Further, in the illustrated embodiment, the bridging regions 22 are staggered in a direction "W" perpendicular to the direction "L" of the interrupted slits 20a.

Figure 1A:
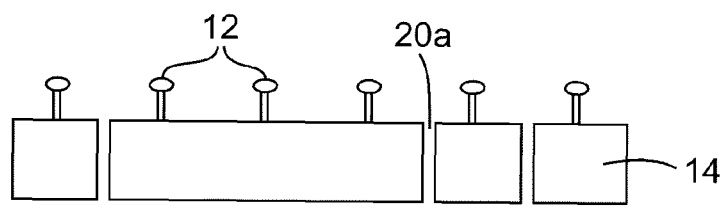
FIG. 1A is a cross-sectional side view taken along line 1AB-1AB of FIG. 1 for one embodiment of a hook strip according to the present disclosure.

A cross-section taken through the hook strip 10 of FIG. 1 at line 1A, 1B-1A, 1B, which extends through the interrupted slits in the slit regions, not the bridging regions, is shown in FIG. 1A. The interrupted slits 20a extend through the backing 14. The interrupted slits 20a are made without removing material from the hook strip but are shown out of scale FIG. 1A to make them more easily visible. In other words, the multiple portions of the backing 14 on either side of the interrupted slits 20a are abutting and not spaced apart.

Figure 1B:
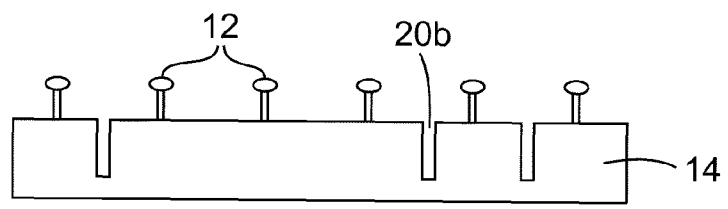
FIG. 1B is a cross-sectional side view taken along line 1AB-1AB of FIG. 1 for another embodiment of a hook strip according to the present disclosure.

The interrupted cutting shown in FIG. 1 to leave bridging regions can also be carried out in embodiments that have partial slits as shown in FIG. 1B. In FIG. 1B, partial slits 20b are cut into the first face of the backing 14 (i.e., the same face from which the hook elements 12 project) between some pairs of adjacent rows 16 of hook elements 12. In the illustrated embodiment, the partial slits 20b are interrupted by bridging regions 22 of the backing 14 that are not slit. The partial slits 20b penetrate the thickness of the backing 14 in a range from 40 to 90 percent. Again, in this embodiment, the partial slits 20b are typically made without removing material from the hook strip but are shown out of scale FIG. 1B to make them more easily visible.

Figure 2:
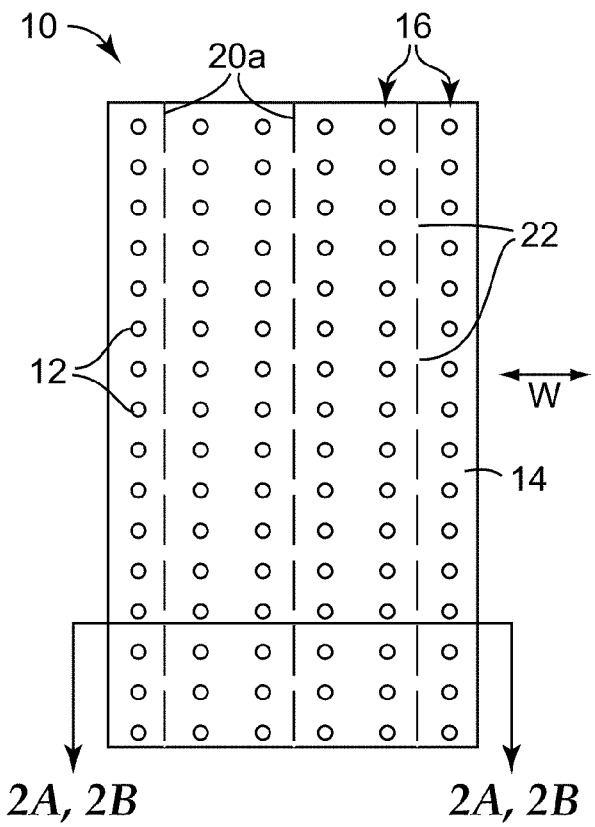
FIG. 2 is a top view of another exemplary hook strip according to the present disclosure.

Another embodiment of a hook strip 10 according to the present disclosure is illustrated in FIG. 2. In this embodiment, two adjacent interrupted slits 20a have two rows 16 of hook elements 12 between them. Furthermore, in FIG. 2, the bridging regions 22 are aligned in a direction "W" perpendicular to the direction of the interrupted slits 20a.

Figure 2A:
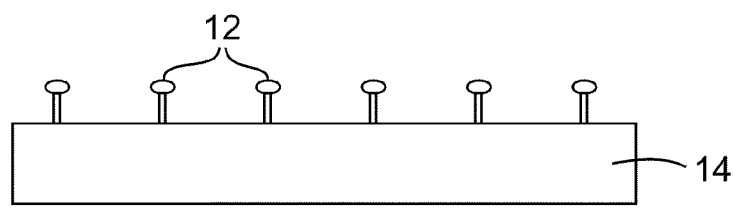
FIG. 2A is a cross-sectional side view taken along line 2AB-2AB of FIG. 2 for some embodiments of a hook strip according to the present disclosure.
Figure 2B:
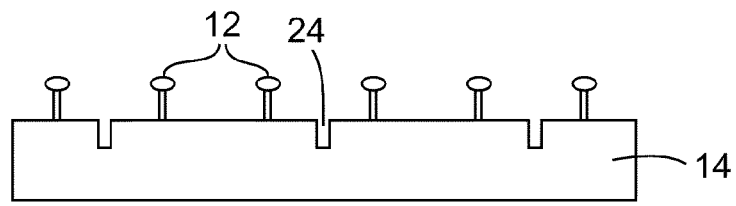
FIG. 2B is a cross-sectional side view taken along line 2AB-2AB of FIG. 2 for other embodiments of a hook strip according to the present disclosure.

Exemplary cross-sections taken through the hook strip 10 of FIG. 2 at line 2A, 2B-2A, 2B, which extends through the aligned bridging regions 22, are shown in FIGS. 2A and 2B. In FIG. 2A, the backing 14 in the bridging regions 22 is uncut. In FIG. 2B, there are partial-depth cuts 24 in the backing 14 in the bridging regions. The partial-depth cuts 24 do not extend through the backing and are collinear with the interrupted slits 20a. The partial-depth cuts 24 may penetrate into the thickness of the backing 14 up to 5, 10, 20, 30, 40, 50, 60, 70, 80, or 90 percent.

Figure 3:
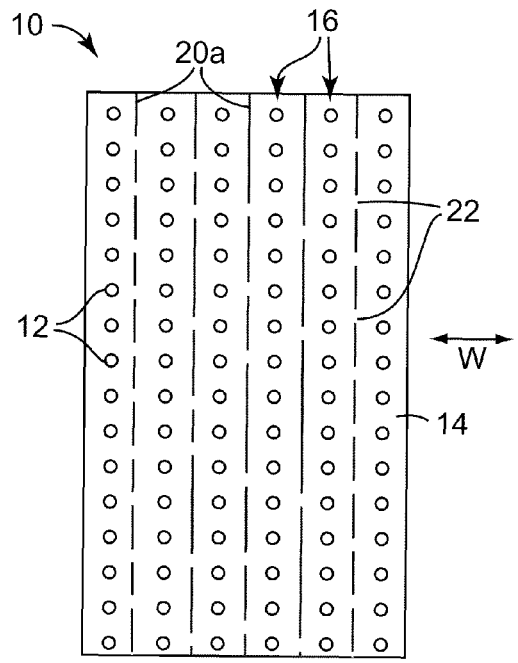
FIG. 3 is a top view of another exemplary hook strip according to the present disclosure.

Another embodiment of a hook strip 10 according to the present disclosure is illustrated in FIG. 3. In this embodiment, there are interrupted slits 20a between every row 16 of hook elements 12. In FIG. 3, the bridging regions 22 are staggered in a direction "W" perpendicular to the direction of the interrupted slits 20a, although in other embodiments, the bridging regions 22 may be aligned. The backing 14 at the bridging regions 22 may be uncut as illustrated above in FIG. 2A, or they may be cut as shown above in FIG. 2B. Interrupted slits 20a are cut through the backing, but the slitting pattern of FIG. 3 can also be useful when partial slits are used. The partial slits do not cut through the backing but penetrate the thickness of the backing 14 in a range from 40 to 90 percent as shown in FIG. 1B.

Figure 4:
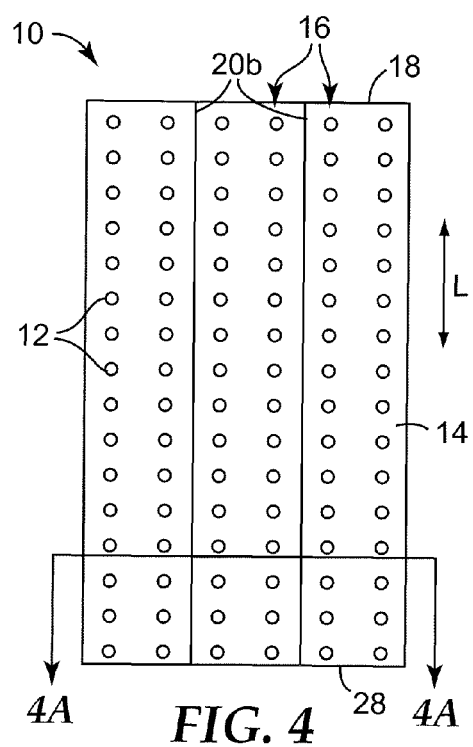
FIG. 4 is a top view of another exemplary hook strip according to the present disclosure.

An embodiment of a hook strip 10 according to the present disclosure having partial slits 20b is shown in FIG. 4. In FIG. 4, hook strip 10 has a backing 14 with multiple rows 16 of hook elements 12 projecting from a first surface of the backing 14. The multiple rows 16 are aligned in at least a first direction; in the illustrated embodiment, the rows 16 of hook elements 12 are aligned in longitudinal direction "L". Partial slits 20b are cut into the backing between some pairs of adjacent rows 16 of hook elements 12. The partial slits 20b are linear in the same direction as the multiple rows 16 and, in the illustrated embodiment, are evenly spaced among the rows 16 of hook elements 12. The number of rows 16 of hook elements 12 between adjacent partial slits 20b can be modified as shown in FIGS. 1, 2, and 3.

Figure 4A:
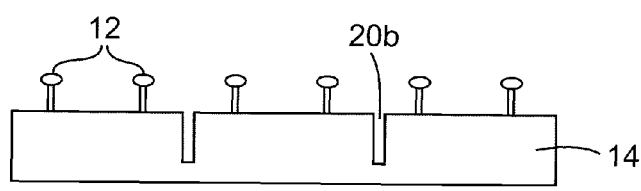
FIG. 4A is a cross-sectional side view taken along line 4A-4A of FIG. 4.

A cross-section taken through the hook strip 10 of FIG. 4 at line 4A-4A is shown in FIG. 4A. The partial slits 20b do not cut through the backing 14 but penetrate the thickness of the backing 14 in a range from 40 to 90 percent. When the partial slits 20b penetrate the thickness of the backing 14 in a range from 40 to 90 percent, the partial slits allow bending between the adjacent rows 16 of hook elements 12, but the backing 14 is not easily ruptured. In some embodiments, the partial slits 20b penetrate the thickness of the backing 14 in a range from 50 to 90, 50 to 85, 55 to 85, 60 to 80, or 65 to 80 percent.

For any of the embodiments of hook strips illustrated in FIGS. 1 to 4, the multiple rows 16 of hook elements 12 may be evenly spaced. For multiple rows 16 that are evenly spaced, the spacing (e.g., distance in the direction "W") between multiple rows 16 may differ by up to 10, 5, 2.5, or 1 percent. Furthermore, in some embodiments, including any of the embodiments described above in connection with FIGS. 1 to 4, backing 14 has a top edge 18 and a bottom edge 28 and the interrupted slits 20a or partial slits 20b extend from the top edge 18 to the bottom edge 28 of the backing.

For any of the embodiments of hook strips illustrated in FIGS. 1 to 4, the hook strip may be in the form of a roll, from which hook patches are cut in a size appropriate to the desired application. In this application, the hook strip may also be a patch that has been cut to a desired size. The bridging regions 22 interrupting the interrupted slits 20a allow the hook strip to be handled as an integral unit. Similarly, because the partial slits 20b do not extend through the backing 14, the hook strip 10 of FIG. 4 may be handled as an integral unit. The bridging regions 22 in any of the embodiments that contain them or the uncut portion of the backing in the embodiments having partial slits allow hook strips according to the present disclosure to be handled in roll form and converted as desired. Accordingly, in some embodiments, the backing 14 is not joined to a carrier, at least when it is initially formed. When the backing 14 is not joined to a carrier, it may mean that the backing is not laminated (e.g., extrusion laminated), adhered, bonded (e.g., ultrasonic bonded or compression bonded) or otherwise attached to a carrier (e.g., a substrate, fastening tab, fastening tape, etc.). Since, in some embodiments, the hook strip according to the present disclosure may be made without being joined to a carrier, there is great flexibility in how the hook strip may be converted and subsequently attached to an article to be fastened.

On the other hand, the hook strip according to the present disclosure may be useful in a fastening laminate. The fastening laminate may be a fastening tab comprising the hook strip disclosed herein in any of the aforementioned embodiments, or the fastening laminate may comprise a hook strip joined to the backsheet of an absorbent article. In some embodiments, the fastening laminate is useful for joining the front waist region and the rear waist region of an absorbent article. The fastening laminate may comprise a carrier and a hook strip disclosed herein, wherein the second surface of the hook strip (i.e., the face opposite the hook elements) is joined to the carrier. The hook strip may be joined to a carrier, for example, by lamination (e.g., extrusion lamination), adhesives (e.g., pressure sensitive adhesives), or other bonding methods (e.g., ultrasonic bonding, compression bonding, or surface bonding).

The carrier may be continuous (i.e., without any through-penetrating holes) or discontinuous (e.g. comprising through-penetrating perforations or pores). The carrier may comprise a variety of suitable materials including woven webs, non-woven webs (e.g., spunbond webs, spunlaced webs, airlaid webs, meltblown web, and bonded carded webs), textiles, plastic films (e.g., single- or multilayered films, coextruded films, laterally laminated films, or films comprising foam layers), and combinations thereof. In some embodiments, the carrier is a fibrous material (e.g., a woven, nonwoven, or knit material). In some embodiments, the carrier comprises multiple layers of nonwoven materials with, for example, at least one layer of a meltblown nonwoven and at least one layer of a spunbonded nonwoven, or any other suitable combination of nonwoven materials. For example, the carrier may be a spunbond-meltbond-spunbond, spunbond-spunbond, or spunbond-spunbond-spunbond multilayer material. Or, the carrier may be a composite web comprising a nonwoven layer and a dense film layer.

Fibrous materials that provide useful carriers may be made of natural fibers (e.g., wood or cotton fibers), synthetic fibers (e.g., thermoplastic fibers), or a combination of natural and synthetic fibers. Exemplary materials for forming thermoplastic fibers include polyolefins (e.g., polyethylene, polypropylene, polybutylene, ethylene copolymers, propylene copolymers, butylene copolymers, and copolymers and blends of these polymers), polyesters, and polyamides. The fibers may also be multi-component fibers, for example, having a core of one thermoplastic material and a sheath of another thermoplastic material.

Useful carriers may have any suitable basis weight or thickness that is desired for a particular application. For a fibrous carrier, the basis weight may range, e.g., from at least about 20, 30, or 40 grams per square meter, up to about 400, 200, or 100 grams per square meter. The carrier may be up to about 5 mm, about 2 mm, or about 1 mm in thickness and/or at least about 0.1, about 0.2, or about 0.5 mm in thickness.

One or more zones of the carrier may comprise one or more elastically extensible materials extending in at least one direction when a force is applied and returning to approximately their original dimension after the force is removed. However, in some embodiments, at least the portion of the carrier joined to the second face of the backing is not stretchable. In some embodiments, the portion of carrier joined to the second face of the backing will have up to a 10 (in some embodiments, up to 9, 8, 7, 6, or 5) percent elongation in the cross direction in the direction perpendicular to the slits (i.e., the width direction (W).

Figure 5:
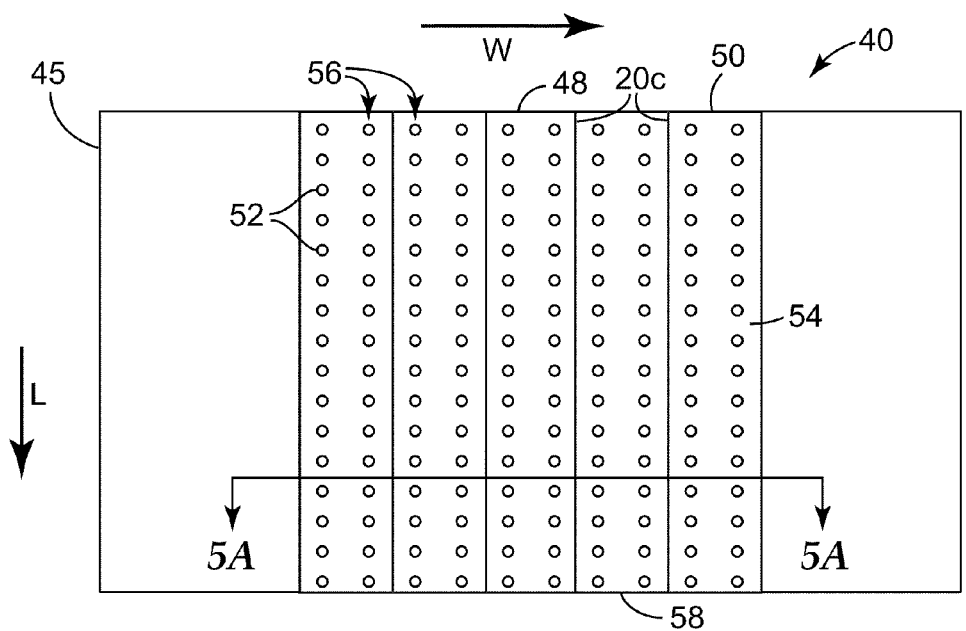
FIG. 5 is a top view of an exemplary fastening laminate according to the present disclosure.

An embodiment of a fastening laminate 40 according to the present disclose is illustrated in FIG. 5. Fastening laminate 40 comprises carrier 45 and hook strip 50. The hook strip has a backing 54 with a first surface having hook elements 52 projecting therefrom and a second surface (not shown) joined to the carrier 45. In the illustrated embodiment, hook elements 52 are in multiple, evenly spaced rows 56 aligned in the first direction, the longitudinal direction "L". Slits 20c are cut through the backing 54 (i.e., through the entire backing thickness) between at least some pairs of adjacent rows 56 of hook elements 52. The slits 20c are linear in the direction of the rows 56 and extend from the top edge 48 to the bottom edge 58 of the backing to form separate, abutting strips of the backing 54 on the carrier 45.

Figure 5A:
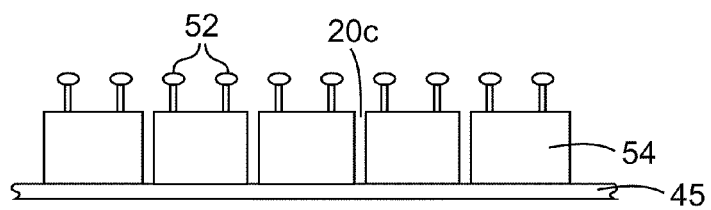
FIG. 5A is a cross-sectional side view taken along line 5A-5A of FIG. 5.

A cross-section taken through laminate 40 of FIG. 5 at line 5A-5A is shown in FIG. 5A. The slits 20c cut through the backing 54 but not the carrier 45. The slits 20c are made without removing material from the hook strip but are shown out of scale FIG. 5A to make them more easily visible. In other words, the multiple strips of the backing 54 are abutting and not spaced apart.

Figure 6:
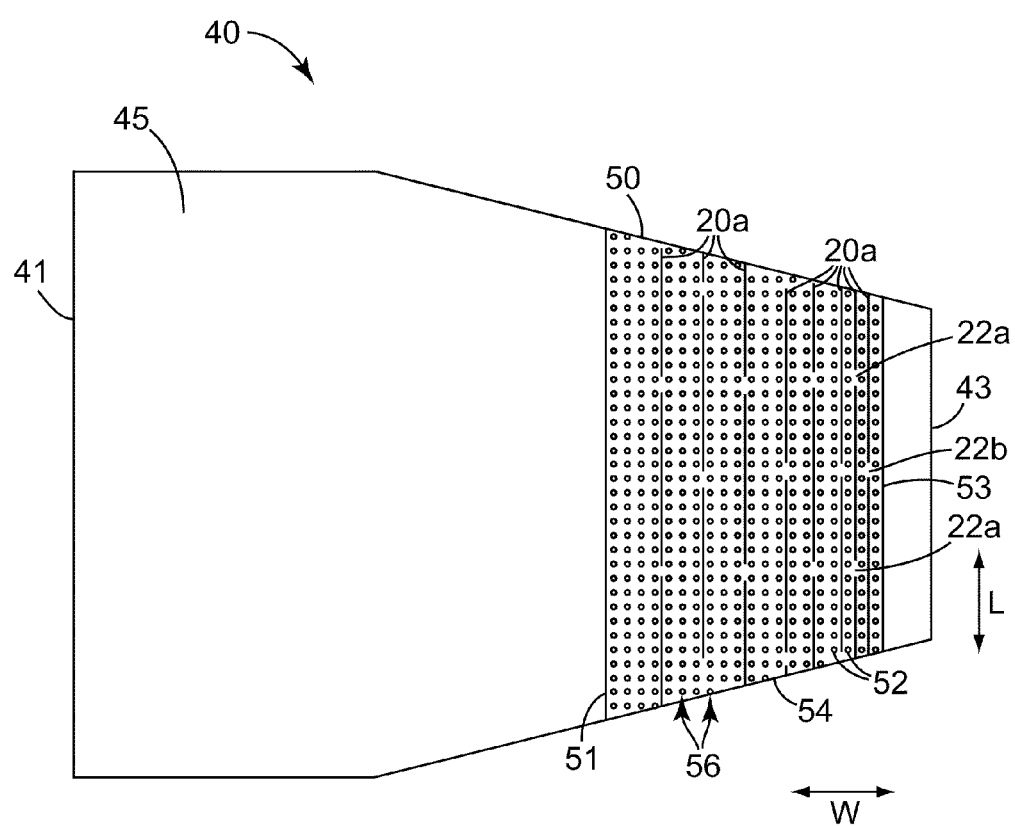
FIG. 6 is a top view of another exemplary fastening laminate according to the present disclosure.

Another fastening laminate 40 according to the present disclosure, comprising carrier 45 and hook strip 50, is illustrated in FIG. 6. Fastening laminate 40 may be a fastening tab (e.g., on an absorbent article) with first edge 41 that may be at the manufacturer's end of the fastening tab (i.e., the end that is permanently fixed to the absorbent article, usually in the waist region) and an opposing second edge 43 that may be at the user's end of the fastening tab (i.e., the end that is grasped by the user). In the embodiment illustrated in FIG. 6, the carrier 45 is shaped such that the second edge 43 is narrower in the longitudinal direction "L" than the first edge 41. The shape of hook strip 50 corresponds to the shape of the carrier 45 with a second edge 53 narrower in the longitudinal direction "L" than a first edge 51. Again second edge 53 of hook strip 50 may be at the user's end of the fastening tab, and first edge 51 may be at the end of the tab permanently attached to the article. Like the embodiment illustrated in FIG. 1, the spacing of the interrupted slits 20a in hook strip 50 is such that the number of rows 56 of hook elements 52 between interrupted slits 20a varies. In should be understood that in order for the number of rows of hook elements between interrupted slits to vary, there should be at least three slits in the backing. In fastening laminate 40, the number of rows 56 of hook elements 52 is smaller toward second edge 53 and larger toward first edge 51. For example, in the illustrated embodiment, there is one row 56 of hook elements 52 between adjacent interrupted slits 20a near the second edge 53 of hook strip 50. As the length of hook strip 50 increases toward the first edge 51 of hook strip 50, the number of rows 56 of hook elements 52 between adjacent interrupted slits 20a increases to 2, then 3, then 4. Although the illustrated embodiment shows interrupted slits 20a, which could have bridging regions in the backing 54 that are cut or not as shown in FIG. 2A or 2B, the shape of the hook strip and configuration of slits and rows 56 is also applicable in embodiments containing partial slits 20b such as those shown in FIG. 4, and slits 20c through the backing that are not interrupted by intact bridging regions such as those shown in FIG. 5.

The tailoring of the number of rows 16, 56 of hook elements 12, 52 between adjacent slits is useful for tailoring the peel force of the hook strip disclosed herein. As described further below in connection with FIGS. 8-11, peel force is typically lowest at low extension when hook and loop fasteners are peeled apart. A low number of rows of hook elements between slits can therefore be very advantageous at the end of a fastening laminate where the peel is initiated. The number of rows of hook elements between slits can be gradually increased toward the trailing edge of the fastening laminate, where the peel force is typically higher. This tailoring may be particularly advantageous, for example, in shaped fastening laminates such as those shown in FIG. 6. In the fastening laminate 40 of FIG. 6, the peel of the fastening laminate is initiated at the narrower, second edge 43, where there are fewer hook elements 52 to engage a loop.

The fastening laminates disclosed herein are useful, for example, in absorbent articles. Absorbent articles according to the present disclosure have at least a front waist region, a rear waist region, and a longitudinal center line bisecting the front waist region and the rear waist region, wherein at least one of the front waist region or the rear waist region comprises the fastening laminate disclosed herein. The fastening laminate may be in the form of a fastening tab that is bonded to at least one of the front waist region or the rear waist region extending outwardly from at least one of the left longitudinal edge or the right longitudinal edge of the absorbent article. In other embodiments, the fastening laminate may be an integral ear portion of the absorbent article. In these embodiments, the first direction (in some embodiments, the machine direction) of the hook strip is generally aligned with the longitudinal center line of the absorbent article.

Figure 7:
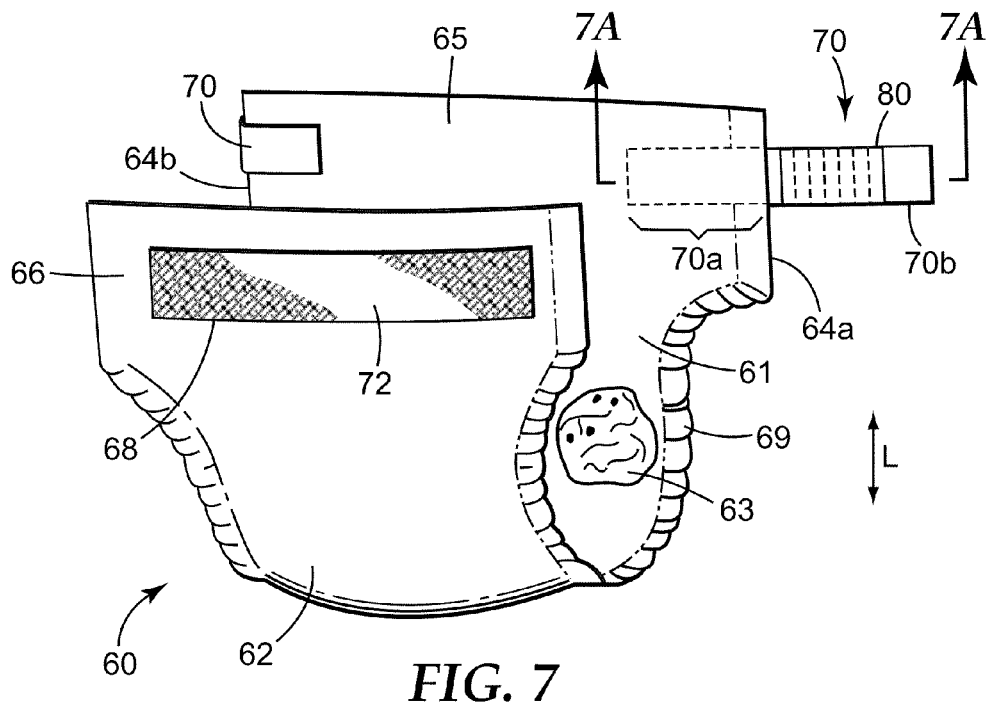
FIG. 7 is a perspective view of an absorbent article incorporating a hook strip according to the present disclosure.

FIG. 7 is a schematic perspective view of a specific embodiment of an absorbent article according to the present disclosure. The absorbent article is a diaper 60 having an essentially hourglass shape. The diaper comprises an absorbent core 63 between a liquid permeable top sheet 61 that contacts the wearer's skin and an outwardly facing liquid impermeable back sheet 62. Diaper 60 has a rear waist region 65 having two fastening tabs 70 arranged at the two longitudinal edges 64a, 64b of diaper 60. The diaper 60 may comprise an elastic material 69 along at least a portion of longitudinal side edges 64a and 64b to provide leg cuffs. The longitudinal direction "L" of the absorbent article (e.g., diaper 60) refers to the direction that the article extends from the front to rear of the user. Therefore, the longitudinal direction refers to the length of the absorbent article between the rear waist region 65 and the front waist region 66. The lateral direction of the absorbent article (e.g., diaper 60) refers to the direction that the article extends from the left side to the right side (or vice versa) of the user (i.e., from longitudinal edge 64a to longitudinal edge 64b in the embodiment of FIG. 7).

In FIG. 7, fastening tabs 70 are secured through their manufacturer's end 70a to the rear waist region 65. The user's end 70b of the fastening tab comprises a hook strip 80 according to the present disclosure. The configuration of hook strip 80 illustrated in FIG. 7 is similar to that shown in FIG. 2, where there are interrupted slits 20a between at least some pairs of adjacent rows of hook elements, and where the bridging regions 22 are aligned. However, the hook strip 80 may also be similar to that shown in any of FIGS. 1 to 6. In some embodiments, when attaching the diaper 60 to a wearer's body, the user's ends 70b of fastening tabs 70 can be attached to a target area 68 comprising fibrous material 72 which may be arranged on the back sheet 62 of the front waist region 66. Examples of loop tapes which may be applied to the target area 68 to provide an exposed fibrous material 72, are disclosed, for example, in U.S. Pat. No. 5,389,416 (Mody et al.) EP 0,341,993 (Gorman et al.) and EP 0,539,504 (Becker et al.). In other embodiments, the back sheet 62 comprises a woven or nonwoven fibrous layer which is capable of interacting with the user's ends 70b of the tape tabs 70 comprising a hook strip disclosed herein. Examples of such back sheets 62 are disclosed, for example, in U.S. Pat. No. 6,190,758 (Stopper) and U.S. Pat. No. 6,075,179 (McCormack et al.). Advantageously, with the improved peel performance of the hook strip according to the present disclosure, adequate fastening between the hook strip 70 and the back sheet 62 may be possible, allowing the elimination of target area 68.

Figure 7A:
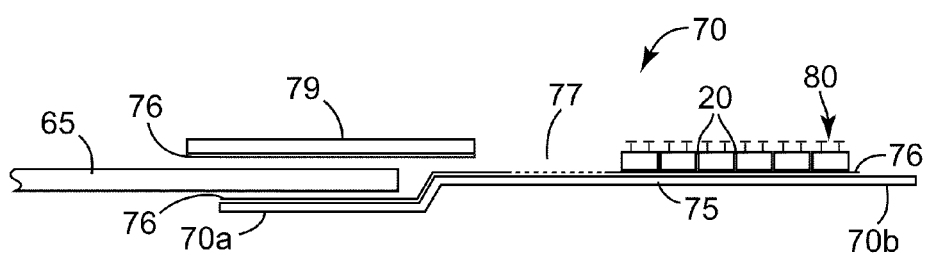
FIG. 7A is an exemplary cross-sectional side view taken along line 7A-7A of FIG. 7.

An exemplary cross-section of the fastening tab 70 taken through line 7A-7A in FIG. 7 is shown in FIG. 7A. Fastening tab 70 has a manufacturer's end 70a for securing it to the diaper rear waist region 65, and a user's end 70b comprising hook strip 80. Fastening tab 70 usually extends beyond longitudinal edges 64a, 64b of the diaper 60. The manufacturer's end 70a corresponds to the part of fastening tab 70 which is fixed or secured to the diaper 60 during the manufacture of the diaper 60. The user's end is typically gripped by the user when attaching the diaper 60 to the wearer and is typically not fixed to the diaper during manufacturing.

In the embodiment illustrated in FIG. 7A, fastening tab 70 comprises a carrier 75 bearing adhesive 76 toward the user's end. Adhesive 76 joins the second face of the backing of the hook strip 80 to the carrier 75 and can be used to join the carrier 75 to the rear waist region 65 of the diaper. Optional exposed adhesive 77 may be present between the hook strip 10 and the diaper rear waist region 65. Fastening tab 70 furthermore optionally comprises release tape 79 to contact the exposed part of adhesive 77 when the hook strip 80 is folded onto diaper rear waist region 65 (e.g., during packaging and shipping of diaper 60). The release tape 79 may also be joined to the diaper rear waist region 65 using adhesive 76. Other configurations of release tape 79 are also possible depending on the configuration of the attachment of the fastening tab 70 to diaper 60. The carrier 75 at the user's end 70b of the fastening tab 70 may exceed the extension of the hook strip 80 and the adhesive 76 thereby providing a fingerlift.

Although the embodiment illustrated in FIG. 7 is an absorbent article with attached fastening tabs, it is envisioned that the hook strip disclosed herein would be equally useful in absorbent articles with larger areas of hooks. For example, the ears of the absorbent article themselves comprise hooks, or the absorbent article can have two target zones of loop material along the longitudinal edges of the back sheet in one waist region and two hook strips extending along the longitudinal edges of the absorbent article in the opposite waist region.

For embodiments that comprises bridging regions 22 (e.g., embodiments such as those illustrated in FIGS. 1, 2, 2A, 2B, 3, 6, and 7), the bridging regions 22 can have the same thickness as the backing (e.g., as in FIG. 2A) or can be thinner than the backing 14. For example, the bridging region 22 may have partial-depth cuts 24 as described above in connection with FIG. 2B, so that the bridging region 22 is thinner than the backing 14.

As described above, bridging regions 22 are useful in embodiments that include interrupted slits through the backing 14 (i.e., through the entire thickness of the backing). Bridging regions 22 are also useful in embodiments that include partial slits that penetrate the thickness of the backing in a range from 40 to 90 percent. In these embodiments, the bridging regions may be uncut or may be cut to an extent less than 40 percent of the thickness of the backing. For any of these embodiments, various lengths of bridging regions 22 may be useful. In some embodiments, any bridging regions between a pair of adjacent rows have a combined length in the first direction of up to 50 (in some embodiments, 40, 30, 25, 20, 15, or 10) percent of the length of the backing in the first direction. In some embodiments, for maximizing the ability of the hook strip to bend, it may be desirable to minimize the combined length of the bridging regions in the first direction. Minimizing the combined length of the bridging regions 22 in the first direction may be accomplished by at least one of minimizing the length of any particular bridging region in the first direction or maximizing the distance between bridging regions 22 on a hook strip. In some embodiments, the length of one bridging region in the first direction is up to 3, 2, or 1.5 mm and at least 0.25, 0.5, or 0.75 mm. In some embodiments, the number of bridging regions along the length of the hook strip in the first direction is up to 1.5, 1.25, 1.0, 0.75, 0.60, or 0.5 per cm. The distance between bridging regions 22 in the first direction may be, for example, at least 0.75, 1.0, 1.25, 1.5, or 1.75 cm. Furthermore, the length of the interrupted slit or partial slit between bridging regions can be adjusted and is typically selected to maximize the distance between bridging regions. In some embodiments, the length of the interrupted slit or partial slit between bridging regions is at least 8 (in some embodiments, at least 10, 12, 14, 15, 16, 17, 18, 19, or 20) mm. Typically, the interrupted slits disclosed herein have longer slit regions and shorter bridging regions than perforations that are designed to allow easy separation of two parts of a film.

Maximizing the distance between bridging regions on a hook strip can be accomplished in some embodiments by staggering the bridging regions as shown in FIGS. 1, 3, and 6. For example, referring again to FIG. 6, the bridging regions 22a and 22b are substantially evenly spaced apart in the first direction "L" but are staggered in the second direction "W", perpendicular to the first direction. The bridging regions 22a and 22b are staggered such that bridging region 22b is located substantially midway between bridging regions 22a in the first direction "L". When the bridging regions are staggered in this manner, the number of bridging regions necessary to make the hook strip handle as an integral unit is minimized. In the hook strip 50 for fastening tab laminate 40, the number of bridging regions 22a and 22b in the interrupted slits 20a alternates between two bridging regions 22a and one bridging region 22b across the hook strip 50.

For any of the embodiments of hook strips, fastening laminates or absorbent articles disclosed herein or the methods of making them, the number of slits (i.e., interrupted slits, partial slits, incomplete slits, or slits that form separate, abutting strips of the backing) may be adjusted depending on the requirements of the application. In some embodiments, there are up to 10, 9, 8, 7, 6, 5, 4, 3, 2, or 1 slits per 10 mm (i.e., interrupted slits, partial slits, incomplete slits, or slits that form separate, abutting strips of the backing) across the width of the strip (i.e., in a direction "W" substantially perpendicular to the first direction or machine direction). As shown in the Examples below, the number of slits (i.e., interrupted slits, partial slits, incomplete slits, or slits that form separate, abutting strips of the backing) in a hook strip according to the present disclosure can affect the peel force that may be achieved, with the area under a peel curve increasing with the number of slits across the hook strip.

Changing the number of slits across the hook strip is related to the number of rows of hook elements between any two adjacent slits, depending on the density of the hook elements on the hook strip. For a hook strip, fastening laminate, absorbent article, or method according to the present disclosure, the density of hook elements 12 on the backing 14 is in a range from 20 per $cm^2$ to 1000 per $cm^2$ (in some embodiments, in a range from 20 per $cm^2$ to 500 per $cm^2$, 50 per $cm^2$ to 500 per $cm^2$, 60 per $cm^2$ to 400 per $cm^2$, 75 per $cm^2$ to 350 per $cm^2$, or 100 per $cm^2$ to 300 per $cm^2$). Advantageously, since the slits are between adjacent rows of hook elements, the incorporation of slits into the hook strips disclosed herein does not decrease the density of hook elements. For any of the embodiments of hook strips, fastening laminates, or absorbent articles disclosed herein or the methods of making them, the number of rows of hook elements between any two adjacent slits (i.e., interrupted slits, partial slits, incomplete slits, or slits that form separate, abutting strips of the backing) may be adjusted depending on the requirements of the application. In some embodiments, there are up to 10, 9, 8, 7, 6, 5, 4, 3, 2, or 1 rows of hook elements between any two adjacent slits (i.e., interrupted slits, partial slits, incomplete slits, or slits that form separate, abutting strips of the backing). In some embodiments, rows of hook elements and slits alternate across the hook strip (i.e., there is a slit between each row of hook elements).

Various shapes of hook elements may be useful for practicing the present disclosure. In some embodiments, all of the hook elements have loop-engaging overhangs. In some of these embodiments, at least a portion of each loop-engaging overhang extends at a nonzero angle to first direction (in some embodiments, the machine direction), which also means that at least a portion of each loop-engaging overhang extends at a nonzero angle to the interrupted slits, partial slits, slits, or incomplete slits. The nonzero angle may be in a range from 30 to 90 degrees, 50 to 90 degrees, 60 to 90 degrees, 75 to 90 degrees, 80 to 90 degrees, or 85 to 90 degrees. The enhanced peel performance that is observed for the hook strips disclosed herein may be most marked when at least a portion of each the loop-engaging overhangs extends in a direction opposite to the direction in which the hook strip is peeled. Accordingly, in an absorbent article disclosed herein at least a portion of each of the loop-engaging overhangs may be directed toward the longitudinal center line of the absorbent article when the absorbent article is fastened around the body. In some embodiments, each hook element has loop engaging overhangs extending in multiple (i.e., at least two) directions. For example, the hook element may be in the shape of a mushroom, a nail, a palm tree, or a T. In some embodiments, the hook element comprises a stem with a mushroom head (e.g., with an oval or round cap).

Figure 8:
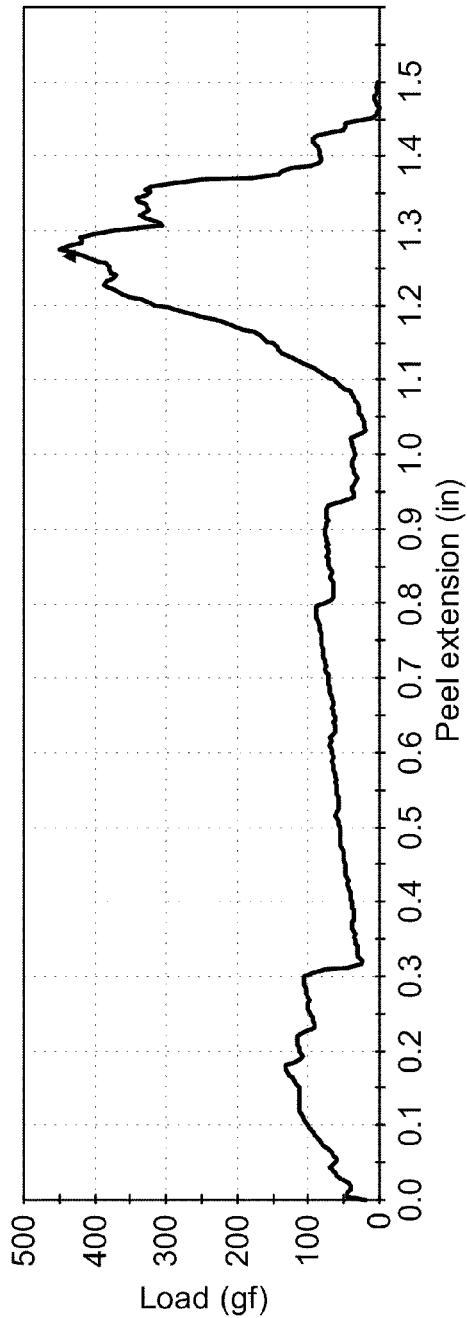
FIG. 8 is a peel curve of a comparative, unslit fastener being removed from a knit loop.

FIG. 8 illustrates a peel curve (i.e., load in grams of force vs. peel extension in inches) of a fastening tab with a comparative hook strip being removed from a knit loop. The comparative hook strip is a conventional hook strip that does not have any slits (i.e., interrupted slits, partial slits, full slits, or incomplete slits) in the backing. The details of the preparation of the fastening tab and the test method are given in the Examples, below. The load at low extension is very low (e.g., up to about 50 grams) and increases as the peel progresses until the force peaks near the end of the hook patch width. A similar result is obtained when evaluating the peel of a comparative hook strip against extrusion bonded loop as the loop material as shown in FIG. 10.

Figure 10:
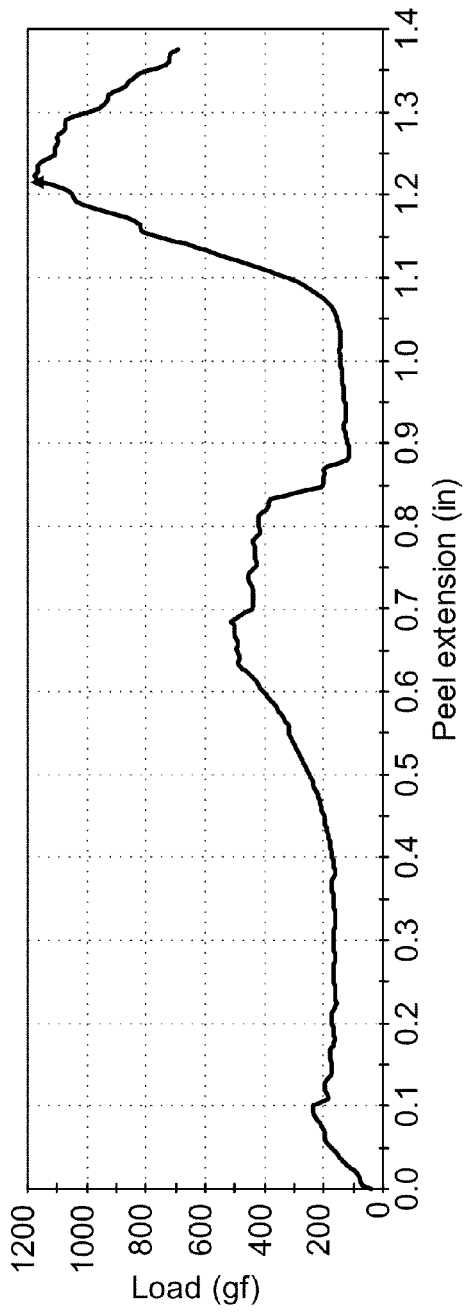
FIG. 10 is a peel curve of a comparative, unslit fastening laminate being removed from a nonwoven loop material.

FIGS. 8 and 10 illustrate that for the conventional hook strip, a substantially constant increase in peel force is required as the hook strip is removed from a loop material. The initial force required to remove the hygiene article closure tab is relatively low, which may affect the actual or perceived reliability of the fastener components. Also, since increasing force is required until the fastener components are completely separated, the amount of force necessary to separate the fastener components may not be readily apparent to the user. The user may also experience an unpleasant sensation when the hook strip is suddenly released from the loop material.

Figure 9:
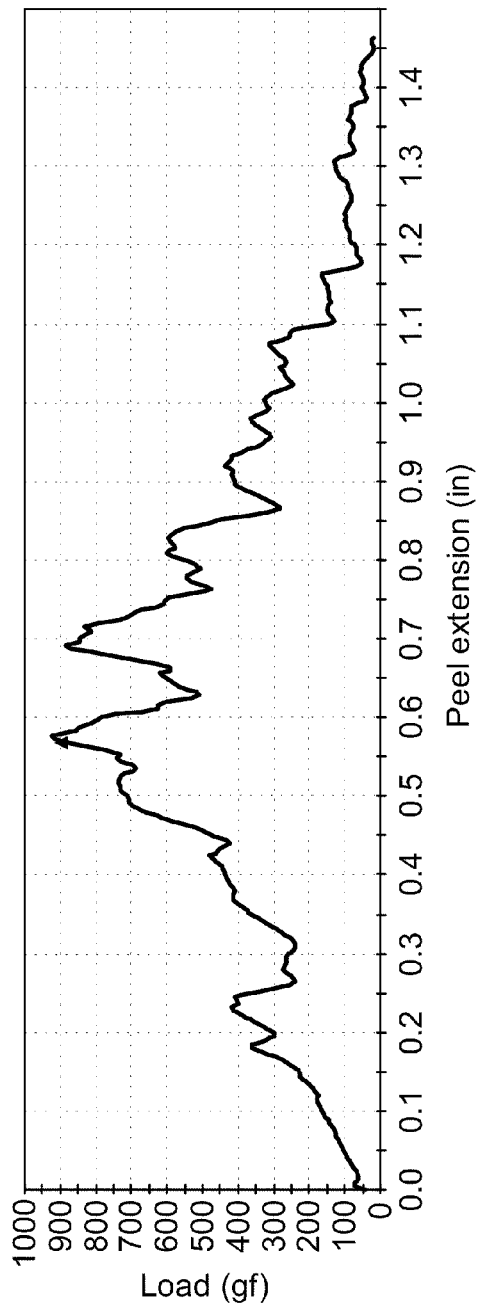
FIG. 9 is a peel curve of a fastening laminate including a specimen of Example Hook Strip 1 being removed from a knit loop.
Figure 11:
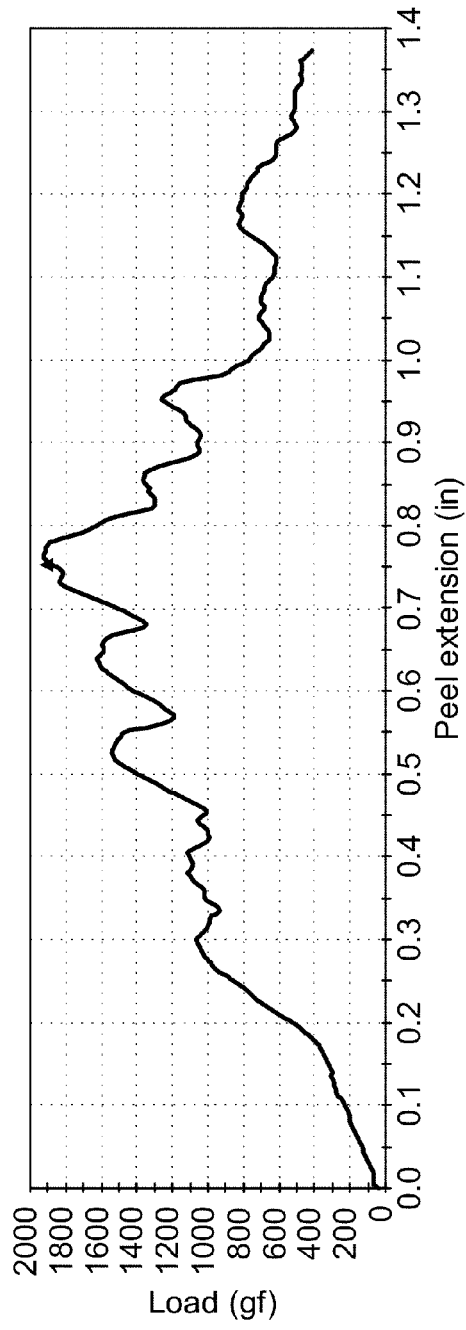
FIG. 11 is a peel curve of a fastening laminate including a specimen of Example Hook Strip 1 being removed from a nonwoven loop material.
Figure 11A:
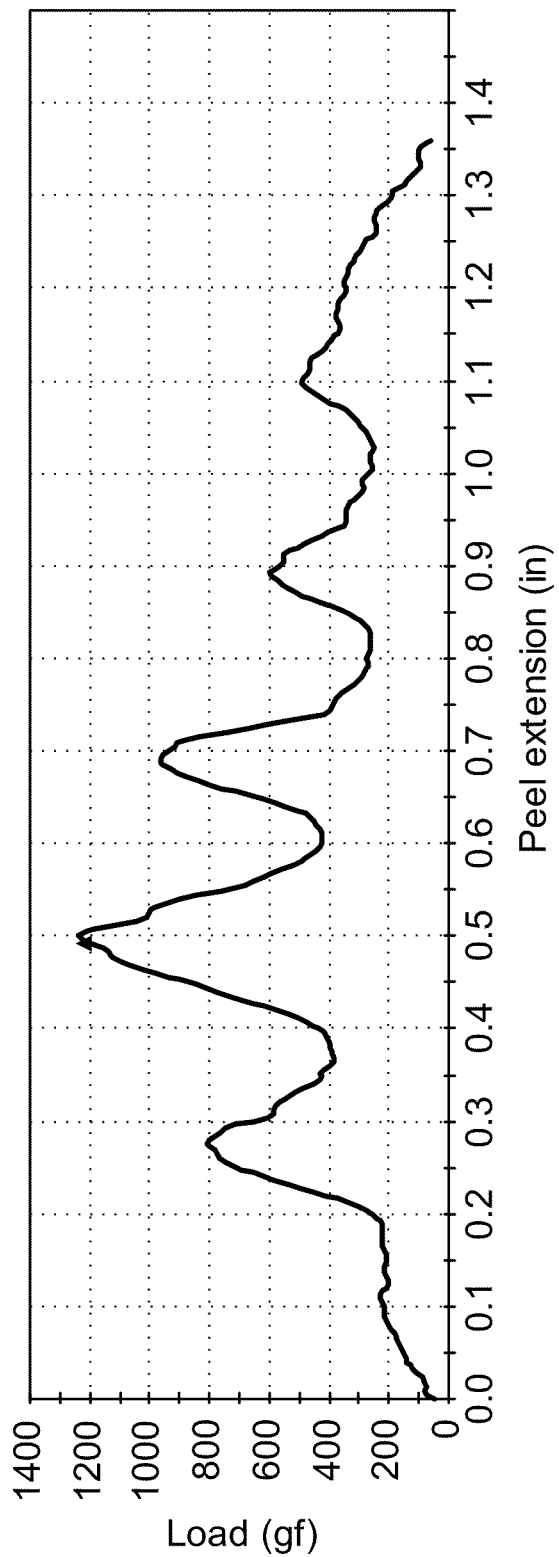
FIG. 11A is a peel curve of a fastening laminate including a specimen of Example Hook Strip 2 being removed from a nonwoven loop material.

FIG. 9 illustrates a peel curve (i.e., load in grams of force vs. peel extension in inches) of a fastening tab with a hook strip according to the present disclosure being removed from a knit loop. The hook strip is the same size as the comparative hook strip, the results of which are shown in FIG. 8, however 7 interrupted slits were cut into the backing between some rows of hook elements. There were 2 rows of hook elements between any two adjacent interrupted slits. The details of the preparation of the fastening tab and the test method are given in the Examples, below. The peel force is much more consistent from the beginning to the end of the peel process and is at a higher force level in comparison to the peel shown in FIG. 8. A similar result is obtained when evaluating the peel of the hook strip according to the present disclosure against extrusion bonded loop as the loop material as shown in FIGS. 11 and 11A. For the specimen that generated the data shown in FIG. 11, there were 2 rows of hook elements between any two adjacent interrupted slits, and for the specimen that generated the data shown in FIG. 11A, there were 4 rows of hook elements between any two interrupted slits.

As shown in FIGS. 8 to 11A, a curve of peel force vs. peel extension has an area under the curve. In some embodiments of the hook strip disclosed herein, when the hook strip is engaged with a loop material, a peel curve defined by load versus peel extension generated upon peeling the hook strip from the loop material has a greater area under the curve than a comparative peel curve generated upon peeling a comparative hook strip from an equivalent loop material, wherein the comparative hook strip is the same as the hook strip except that the comparative hook strip has no slits (e.g., no interrupted slits, partial slits, incomplete slits, or full slits depending on the embodiment). In some embodiments, the area under the curve for the hook strip according to the present disclosure is at least 20, 30, 40, or 50 percent more than the area under the curve for the comparative hook strip. A comparative hook strip is the "same" as the hook strip disclosed herein, except that it has no slits. The comparative hook strip has the same dimensions (e.g., height, width, and thickness), the same hook density, the same hook head shape and dimensions, the same configuration of hooks (e.g., rows), and is made from the same material as the hook strip disclosed herein. An "equivalent" loop material refers to a loop material that is similar to or the same (e.g., in material, loop construction (e.g., knitted, woven, or nonwoven), and dimensions (e.g., height, width, and thickness)) as a loop material from which a hook strip according to the present disclosure is peeled before it is subjected to the peel evaluation.

It is evident from the comparison of FIGS. 8 to 11A, that the force required to remove a hook strip according to the present disclosure is typically, in many embodiments, more uniform throughout the peel extension than for a comparative hook strip. In some embodiments, the area under the curve at one-half of the peel extension is at least 30, 35, 40, or 45 percent of the total area under the curve. In some embodiments, at least 200 grams of force is achieved within the first one-fourth, one-third, or one-half of the peel extension. In some embodiments, at least one peak in the first one-fourth, one-third, or one-half of the peel extension has a value that is at least 50, 60, 70, or 75 percent of the maximum peak value. Furthermore, in some embodiments, at least some points along the curve up to one-half of the maximum peel extension, the peel force required to remove the hook strip according to the present disclosure from a loop material is at least 20, 30, 40, or 50 percent higher than a peel force required to remove a comparative hook strip from an equivalent loop material. The comparative hook strip is the same as the hook strip disclosed herein except that it has no slits.

Enhancements to a conventional hook strip to increase the area under the peel curve may have conventionally involved using more aggressive hooks, for example. More aggressive hooks may lead to a higher maximum load without changing the typical shape of the peel curve of the conventional hook strip that is shown in FIGS. 8 and 10. More aggressive hooks that provide higher maximum loads may increase damage (e.g., fuzzing or fiber breakage) to, for example, a nonwoven loop material, which may inhibit reattachment to the loop material. In contrast, for a hook strip according to the present disclosure, the area under the peel curve can be increased without increasing the maximum load by providing enhanced load at extensions up to one-half the maximum peel extension. Thus, a hook strip according to the present disclosure may advantageously provide enhanced peel performance without causing damage to a loop material.

Figure 12:
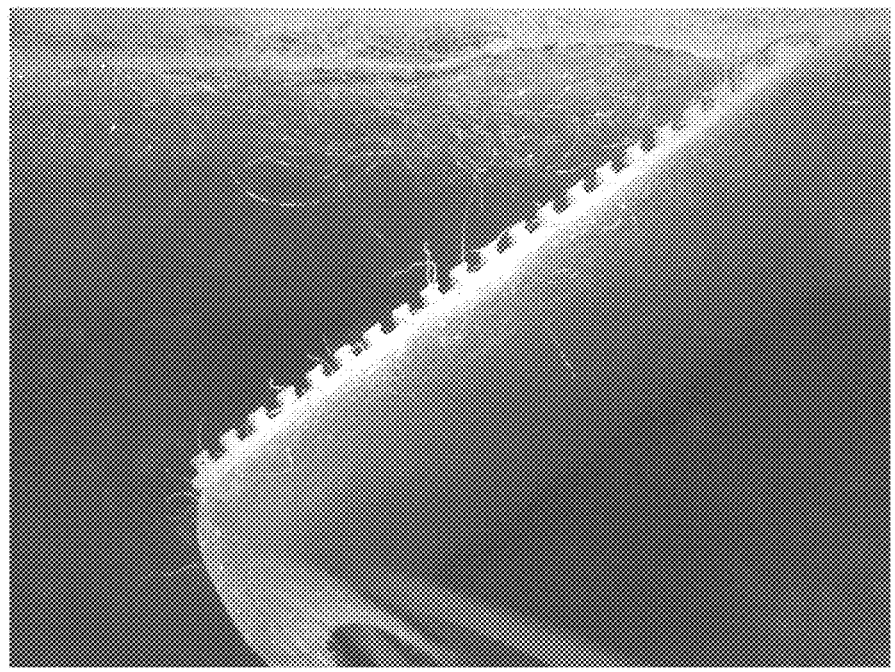
FIG. 12 is a photograph a comparative, unslit fastening laminate as it is peeled from a nonwoven loop material.
Figure 13:
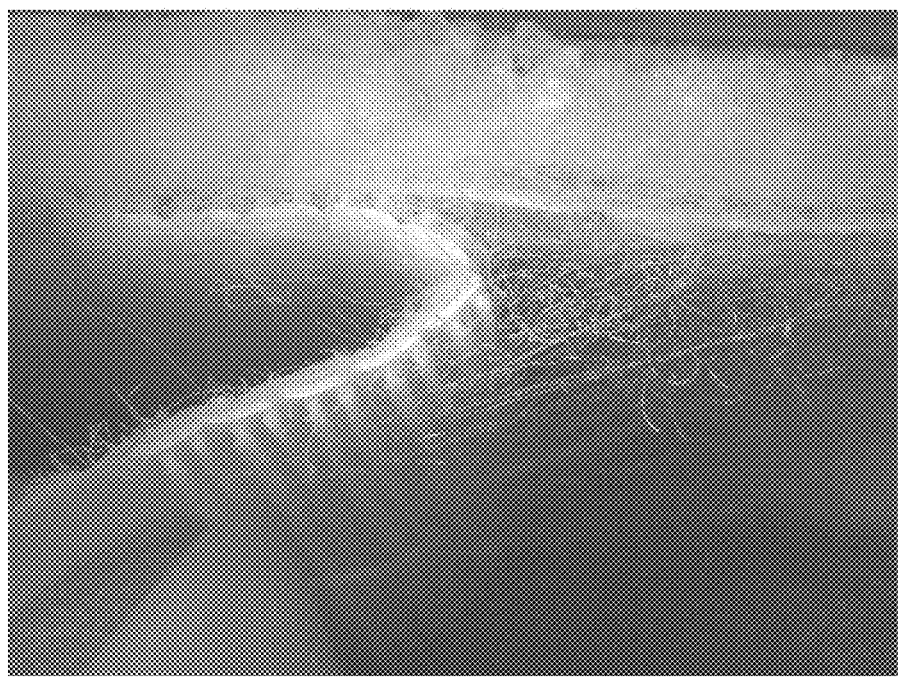
FIG. 13 is a photograph a fastening laminate including a hook strip according to the present disclosure as it is peeled from a nonwoven loop material.

FIG. 12 is a photograph of a comparative, unslit hook fastener as it is peeled from a nonwoven loop material. It is notable that the stiffness of the backing of the comparative hook strip affects the peel angle of individual rows of hook elements. In contrast, FIG. 13 is a photograph of a hook strip according to the present disclosure. The hook strip of FIG. 13 and the comparative hook strip have the same thickness of the backing and the same configuration of hooks, but the hook strip of FIG. 13 has 9 interrupted slits cut into the backing between rows of hook elements. There were about two rows of hook elements between any two adjacent interrupted slits. The interrupted slits allow the peel angle of individual rows of hook elements to increase, and the individual rows of hook elements are allowed to pivot to provide an increased percentage of loop engagements. It is also possible that the ability for the rows of hook elements between slits to pivot can allow the loops to slide down further onto the stem of the hook elements. In any case, it is apparent from the photographs that there is much more interaction between the hook elements and the loop material in FIG. 13 than in FIG. 12. In some embodiments of the hook strip disclosed herein, when the hook strip is engaged with a loop material and then peeled from the loop material at a peel angle of 135 to 180 degrees, a peel angle of an individual row of hook elements at a distance from a peel front is greater (in some embodiments, at least 10, 20, 30, 40, or 50 degrees more) than a peel angle of an individual row of hook elements in a comparative hook strip at the distance from the peel front when the comparative hook strip is peeled from an equivalent loop material, wherein the comparative hook strip is the same as the hook strip except that the comparative hook strip has no slits (e.g., no interrupted slits, partial slits, incomplete slits, or full slits depending on the embodiment). The peel angle refers to the angle between the stem of the hook element and the surface of the loop material. In some embodiments, the distance from the peel front (i.e., the point of separation between the hook strip and the loop material) is 1, 2, 3, 4, or 5 mm.

Hook strips with lower caliper backings can bend more than the comparative hook strip shown in FIG. 12, and, depending on the selection of the loop material, the difference in peel performance in a laboratory 135 to 180 degree peel test between a hook strip according to the present disclosure and a comparative hook strip with a thinner backing (e.g., up to 50, 80. or 90 micrometers) is not as pronounced. However, typically a user peeling a hook strip according to the present disclosure and a comparative hook strip that is not slit can still perceive a difference regardless of the thickness of the backing.

The hook strip according to the present disclosure is typically made of a thermoplastic material. Suitable thermoplastic materials for the hook strip include polyolefin homopolymers such as polyethylene and polypropylene, copolymers of ethylene, propylene and/or butylene; copolymers containing ethylene such as ethylene vinyl acetate and ethylene acrylic acid; polyesters such as poly(ethylene terephthalate), polyethylene butyrate and polyethylene napthalate; polyamides such as poly(hexamethylene adipamide); polyurethanes; polycarbonates; poly(vinyl alcohol); ketones such as polyetheretherketone; polyphenylene sulfide; and mixtures thereof. Typically, the hook strip is made of a polyolefin (e.g., polyethylene, polypropylene, polybutylene, ethylene copolymers, propylene copolymers, butylene copolymers, and copolymers and blends of these materials).

In the hook strips disclosed herein the backing and the hook elements are typically integral (that is, formed at the same time as a unit, unitary). Hook elements on a backing can be made, for example, by feeding a thermoplastic material onto a continuously moving mold surface with cavities having the inverse shape of the hook elements. The thermoplastic material can be passed between a nip formed by two rolls or a nip between a die face and roll surface, with at least one of the rolls having the cavities. The cavities may be in the inverse shape of a hook element having a loop-engaging head or may be in the inverse shape of a stem or of a partially formed hook element (e.g., a precursor to a hook element). In the methods disclosed herein, the term "hook element" is meant to include stems without heads. Pressure provided by the nip forces the resin into the cavities. In some embodiments, a vacuum can be used to evacuate the cavities for easier extrusion into the cavities. The nip is typically sufficiently wide such that a coherent backing is formed over the cavities. The mold surface and cavities can optionally be air or water cooled before stripping the integrally formed backing and upstanding hook elements from the mold surface such as by a stripper roll. If the hook elements formed upon exiting the cavities do not have loop-engaging heads, loop-engaging heads could be subsequently formed into hooks by a capping method as described in U.S. Pat. No. 5,077,870 (Melbye et al.), the disclosure of which is incorporated herein by reference in its entirety. Typically, the capping method includes deforming the tip portions of the hook elements using heat and/or pressure. The heat and pressure, if both are used, could be applied sequentially or simultaneously.

Another useful method for forming hook elements on a backing is profile extrusion described, for example, in U.S. Pat. No. 4,894,060 (Nestegard), which is incorporated herein by reference in its entirety. Typically, in this method a thermoplastic flow stream is passed through a patterned die lip (e.g., cut by electron discharge machining) to form a web having downweb ridges, slicing the ridges, and stretching the web to form separated projections. The ridges may form hook precursors and exhibit the cross-sectional shape of hook elements (e.g., with loop-engaging heads) to be formed. The ridges are transversely sliced at spaced locations along the extension of the ridges to form discrete portions of the ridges having lengths in the direction of the ridges essentially corresponding to the length of the hook elements to be formed.

Some hook strips which may be useful precursors for the hook strip according to the present disclosure are commercially available, e.g., from 3M Company, St. Paul, under the trade designations "CS-600" or "CS-1010".

For the hook strip according to the present disclosure in any of its various embodiments, the thickness of the backing may be up to about 400, 250, 150, 100, 75 or 50 micrometers, depending on the desired application. In some embodiments, the thickness of the backing is in a range from 30 to about 225 micrometers, from about 50 to about 200 micrometers, or from about 100 to about 150 micrometers. In some embodiments, the hook elements have a maximum height (above the backing) of up to 3 mm, 1.5 mm, 1 mm, or 0.5 mm and, in some embodiments a minimum height of at least 0.05 mm, 0.1 mm, or 0.2 mm. In some embodiments, the hook elements have aspect ratio (that is, a ratio of height to width at the widest point) of at least about 2:1, 3:1, or 4:1.

Slits in the backing (e.g., interrupted slits, partial slits, slits that form separate, abutting strips of the backing, and incomplete slits) can be formed, for example, using rotary die cutting of a continuous web having a backing and hook elements formed by any of the methods described above. Interrupted slits can be made, for example, by using rotary cutting blades having gaps to form the bridging regions. The height of the blade in the gaps may be adjusted to allow for the bridging regions to be partially cut or not cut at all, depending on the desired embodiment. Partial slits can be made, for example, by adjusting the heights of the blades of the rotary die to make slits of the desired depth. Other cutting methods (e.g., laser cutting) may also be used. For interrupted or non-interrupted slits through the backing, the cutting can be performed from either surface of the continuous web, corresponding to the first surface or second surface of the backing. For partial slits, the slits are made in the first surface of the backing, which is the same surface from which the hook elements project. When the hook elements are formed using the method described above, where a thermoplastic material is fed onto a continuously moving mold surface with cavities having the inverse shape of the hook elements with loop-engaging heads, the slits can be made in the web before or after a capping step is carried out to form loop-engaging heads. It should be understood that cutting methods disclosed herein on a continuous web may result in some instances with slits that cross over or cut through a row of hook elements. Although the rotary die, for example, may be positioned to form a slit between rows of hook elements, the variability in the web process may cause the slit to cross over a row of hook elements and later return to its intended position.

For embodiments of hook strips disclosed herein having partial slits, the partial slits may also be made using raised ridges on the roll formed with the cavities having the inverse shape of the hook elements to be formed. Or the profiled die lip used in the profile extrusion method can be made to form depressions in the backing. In these embodiments, the slits are formed simultaneously with the hook elements during the molding or extrusion process.

In embodiments where there is stretched-induced molecular orientation in the backing, stretching can be carried out on a web biaxially or monoaxially using techniques known in the art. For example, stretching can be carried out in a flat film tenter stretching apparatus, or monoaxial stretching can be carried out by passing the continuous web laminate in the machine direction over rollers of increasing speed. Stretching can be carried out before or after slits are made in the backing.

Methods of making multiple hook strips according to the present disclosure include forming a continuous web having a backing and multiple rows of hook elements aligned in rows in a machine direction and projecting from a first surface of the backing using, for example, any of the methods described above; cutting incomplete slits (i.e., interrupted slits, partial slits, or a combination thereof) in the machine direction in the backing between at least some pairs of adjacent rows of the hook elements, wherein the incomplete slits do not sever the backing; and cutting complete slits in the machine direction through the backing. Cutting the incomplete slits and cutting the complete slits can be carried out sequentially or simultaneously. In some embodiments of the method disclosed herein, the incomplete slits and complete slits are cut into the continuous web, simultaneously or sequentially, and the resulting multiple hook strips according to the present disclosure are individually wound (e.g., level wound) into rolls. The hook strips can optionally later be joined to a carrier, if desired, or otherwise converted.

In some embodiments of the method disclosed herein for forming multiple hook strips according to the present disclosure, the complete slits are cut into the continuous web first to provide multiple strips. The multiple strips are then joined to a carrier (e.g., a web of any of the carriers described above). The laminated multiple strips may optionally be wound into a roll before partial depth cutting is used to make incomplete slits (i.e., interrupted or partial slits) in the backing without cutting the carrier. In yet other embodiments of the method described herein, the complete slits are first cut into the continuous web first to provide multiple strips, which optionally may be wound into individual rolls or otherwise stored. Subsequently, incomplete slits may be cut into the multiple strips, for example, immediately before joining to a carrier (e.g., a web of any of the carriers described above).

For embodiments of the laminate disclosed herein, wherein the slits extend in the first direction from the top edge to the bottom edge of the backing to form separate, abutting strips of the backing on the carrier, the slits are typically formed by rotary cutting or laser cutting after the backing is joined to the carrier.

In any of the embodiments where the second surface of the backing is joined to a carrier, the joining can be carried out using adhesives (e.g., pressure sensitive adhesives). In embodiments where interrupted slits are made in the backing before the second surface of the backing is joined to an adhesive, the viscosity of the pressure sensitive adhesive may be selected so that it does not go through the slits during the joining process.

In some embodiments where the carrier is a fibrous web, the joining comprises impinging heated gaseous fluid (e.g., ambient air, dehumidified air, nitrogen, an inert gas, or other gas mixture) onto a first surface of the fibrous web while it is moving; impinging heated fluid onto the second surface of the backing while the continuous web is moving, wherein the second surface is opposite the first surface of the backing; and contacting the first surface of the fibrous web with the second surface of the backing so that the first surface of the fibrous web is melt-bonded (e.g., surface-bonded or bonded with a loft-retaining bond) to the second surface of the backing. Impinging heated gaseous fluid onto the first surface of the fibrous web and impinging heated gaseous fluid on the second surface of the backing may be carried out sequentially or simultaneously.

Melt-bonding (e.g., surface-bonding or loft-retaining bonding) using heated gaseous fluid may be carried out, for example, by passing a fibrous web and the continuous web comprising the backing and the hook elements through a nip formed by two backing rolls. The fibrous web and the continuous web comprising the backing and the hook elements generally are fed into the nip from two different directions and contact each other in the nip. The backing rolls may be arranged so as to operate the nip at very low pressure (e.g., less than about 15 pounds per linear inch (27 Newtons per linear cm), less than about 10 pli (18 Nlc), or less than about 5 pli (9 Nlc)) in comparison to the pressures normally used in the lamination of materials (for which relatively high pressure is often preferred). In some embodiments, at least one of the backing rolls may comprise at least a surface layer of a relatively soft material (e.g., a rubber material with a hardness of less than 70 on the Shore A scale). Such a relatively soft surface layer may be achieved, for example, by the use of a roll with a permanently attached soft surface coating, by the use of a removable sleeve of soft material, or by covering the surface of the backing roll with relatively soft and resilient tape. If desired, the surface of one or both backing rolls may be stepped across the face of the roll so as to provide lamination pressure selectively in certain locations. Heated gaseous fluid may be impinged on the two webs, for example, using a nozzle that is placed close to the nip. The nozzle may be configured to have a first fluid delivery outlet and a second fluid delivery outlet that are in diverging relation (e.g., the flow paths from the first and second delivery outlets differ by at least 25 degrees) to deliver heated gaseous fluid to the two different webs. The fluid may be heated by an external heater before being delivered to the nozzle through a supply line. In addition or instead, heating elements may be supplied within the nozzle, or additional heating (e.g., resistance heating or infrared heating) of the nozzle may be applied. In some embodiments, the impinged heated fluid is locally captured by way of at least one first fluid capture inlet that is locally positioned with regard to the first fluid delivery outlet, and at least one second fluid capture inlet that is locally positioned with regard to the second fluid delivery outlet. Joining the continuous web to a fibrous web using this method may be advantageous, for example, for maintaining the shape of the hook elements and without damaging any of the interrupted or partial slits or bridging regions when the continuous web and the carrier are joined together.

Surface-bonding or loft-retaining bonding may be advantageously performed over a large area or areas (herein termed "area-bonding") in contrast to the small-area bonding (often called point-bonding) that is often achieved by ultrasonic bonding or other melt-bonding processes. The large number of surface-bonded fiber portions that may be randomly and/or uniformly present over the bonded area in such area-bonding can collectively provide adequate bond strength for laminate to be handled and to perform satisfactorily in various end uses. In some embodiments, area-bonds occupy at least about 100 square mm, at least about 400 square mm, or at least 1000 square mm.

Further methods and apparatus for joining a continuous web to a fibrous carrier web using heated gaseous fluid may be found in co-pending U.S. Patent Applications with Ser. Nos. 61/288,952 and 61/288,959, both filed Dec. 22, 2009, and incorporated herein by reference in their entirety.

In order that this disclosure can be more fully understood, the following examples are set forth. It should be understood that these examples are for illustrative purposes only, and are not to be construed as limiting this disclosure in any manner.

EXAMPLES

Hook Strips

Control hook strips were prepared using the methods described in U.S. Pat. No. 5,077,870 (Melbye et al.) and U.S.

Pat. No. 6,132,660 (Kampfer). The polymer used to prepare the hook strips was an ethylene-propylene copolymer available from Dow Chemical Co., Midland, Mich., under the trade designation "C700-35N". The basis weight of the hook strips was 191 grams per square meter (gsm) and the hook density was 1600 hooks per inch$^2$ (248 cm$^2$) arranged in a square array. The total caliper of the hook strips was 525 micrometers (μm) with a base film (backing) caliper of 180 μm. The cap shape of the hook elements was oval (270 μm in the machine direction of the hook making process and 420 μm in the cross direction of the hook making process). Example Hook Strip 1 and Example Hook Strip 2 were prepared using the same hook material as the control hook strips. A plurality of interrupted slits were made extending through the thickness of the hook strip backing at spaced locations in the machine direction of the hook making process using a rotary cutting blade. Example Hook Strip 1 had interrupted slits located between every two rows of hook elements. Example Hook Strip 2 had interrupted slits located between every four rows of hook elements. For both hook strips the slits were 0.71 inch (18 mm) long and the slits were interrupted by intact bridging regions that were 0.04 inch (1 mm) long. The bridging regions were staggered in a direction perpendicular to the direction of interrupted slits as shown in FIG. 6. The other dimensions and characteristics of Example Hook Strips 1 and 2 (e.g., basis weight, hook density, total caliper, backing caliper, cap shape and dimensions, etc.) were the same as the control hook strip.

180 Degree Peel Evaluation

The 180 Degree Peel Evaluation was used to examine the peel characteristics when removing the control hook strips and Example Hook Strips 1 and 2 from various loop fastener materials.

Hook fastener tabs were prepared for the peel evaluation by removing the hook materials from the nonwoven carrier of the fastening tabs on "PAMPERS BABY DRY" size 4 diapers (Procter & Gamble Company). This was done by cooling the tabs by exposure to liquid nitrogen and peeling the existing hook piece off of the nonwoven carrier while cold, and when the nonwoven carrier had warmed to room temperature, pieces of the control hook strips and Example Hook Strips 1 and 2 (13 mm×25.4 mm in size) were then placed on the nonwoven carrier of the diaper fastening tab using two layers of a double coated adhesive tape obtained from 3M Company, St. Paul, Minn., under the trade designation "SCOTCH ADHESIVE TRANSFER TAPE NO. 924", leaving enough adhesive exposed (about 6 mm) to allow the hook fastener tab to be attached to a paper leader for peel evaluation (this is the existing exposed adhesive of the nonwoven fastener tab).

The loop samples used for peel evaluation were obtained by removing loop fastener patches from commercially available baby diapers. Loop A (knit loop) was obtained from Size 4 diapers available from Procter & Gamble Company under the trade designation "PAMPERS BABY DRY". Loop B (extrusion bonded loop, such as described in U.S. Pat. No. 5,256,231 (Gorman et al.) was obtained from New Baby Size 1 diapers available from Procter & Gamble Company under the trade designation "PAMPERS SWADDLERS". Loop C (nonwoven loop) was obtained from size 4 baby diapers available from (Procter & Gamble Company) under the trade designation "LUVS".

The peel evaluations were carried out at constant temperature and humidity (23° C. and 51% relative humidity). The loop material used for testing was securely placed onto a 2 inch×5 inch (5.08 cm×12.7 cm) steel panel using double coated adhesive tape. The hook fastener tab prepared as described above was attached to a 1 inch×8 inch (2.54 cm×20.3 cm) paper leader using the exposed adhesive on the hook fastener tab. The hooks were placed on either end of the loop material (tails off each end). This was done due to the directionality of the knit loop material, and the other loop materials were tested in the same manner. The samples were rolled down by hand with a 4.5 lb (2 kg) rubber roller two times (four passes, top down). The loop panel was placed in the bottom jaw of an "INSTRON" constant rate of extension tensile tester and the end of the paper leader attached to the hook fastener was placed in the top jaw (8 inch (20.3 cm) jaw gap). At a crosshead speed of 12 inches (30.5 cm) per minute, the peel was recorded, maintaining the peel angle at 180 degrees, until the hook strip disengaged from the loop material. The results are reported in the Tables 1 to 3. The top jaw traveled until the hook tab was completely disengaged from the loop.

Table 1 summarizes the 180 degree peel data obtained when evaluating the hook strips using Loop A (knit loop). FIG. 8 illustrates the peel curve for Control Example Specimen C2. Similar peel curves (not shown) were obtained for Control Example Specimens C1 and C3. The load at low extension is low (first half of the curve) and then increases towards the end of the hook patch (second half of the peel curve). It was observed that these peels curves were typical of peel curves for the control hook strips being removed from a knit loop material. FIG. 9 illustrates the peel curve for Specimen 2 of Example Hook Strip 1, a hook strip having interrupted slits cut into the backing between every two rows of hook elements. Similar peel curves (not shown) were obtained for Specimens 1 and 3. The peel force was more consistent throughout the peel curve and was at a higher force level in comparison to the peel curve shown in FIG. 8. It was observed that these peels curves were typical of peel curves for hook strips according to the present disclosure being removed from a knit loop material. In the following tables, Delta Energy describes the area under the peel curve.

TABLE 1

| Specimen | Hook Strip | Delta Energy millijoule (mJ) | Max Load gram-force (gf) | Avg. Load (gf) | Avg. Peak (gf) |
|---|---|---|---|---|---|
| C1 | Control | 27.5 | 337.9 | 77.7 | 169.7 |
| C2 | Control | 39.6 | 450.1 | 106.1 | 172.9 |
| C3 | Control | 27.5 | 396.9 | 87.4 | 130.2 |
| 1 | Ex. 1 | 108.6 | 706.0 | 325.2 | 454.1 |
| 2 | Ex. 1 | 125.6 | 922.9 | 344.6 | 469.5 |
| 3 | Ex. 1 | 148.2 | 1011.6 | 416.9 | 570.3 |

Table 2 summarizes the 180 degree peel data obtained when evaluating the hook strips using Loop B (extrusion bonded loop). FIG. 10 illustrates the peel curve for Control Example Specimen C5. Similar peel curves (not shown) were obtained for Control Examples Specimens C4 and C6. The results were similar to that obtained when evaluating the control hook strip with the knit loop material as described above. The load at low extension is low (first half of the curve) and then increases towards the end of the hook patch (second half of the peel curve). It was observed that these peel curves were typical of peel curves for the control hook strips being removed from an extrusion bonded loop material. FIG. 11 illustrates the peel curve for Specimen 4 of Example Hook Strip 1. Similar peel curves (not shown) were obtained for Specimens 5 and 6. The results obtained were similar to those obtained for evaluating the Example Hook Strip 1 with the knit loop material as described above. The peel force was more consistent throughout the peel curve and was at a higher force level in comparison to the peel curve shown in FIG. 10.

It was observed that these peel curves were typical of peel curves for hook strips according to the present disclosure being removed from an extrusion bonded loop material. Example Hook Strip 2, a hook strip having interrupted slits cut into the backing between every four rows of hook elements, was used for Specimens 7-9. FIG. 11A illustrates the peel curve for Specimen 9. Similar peel curves (not shown) were obtained for Specimens 7 and 8. While differences between these examples and the control hook strips are not be readily apparent from the tabulated data, it is evident from comparing the peel curve shapes of FIG. 10 and FIG. 11A that the force required to remove Example Hook Strip 2 from the extrusion bonded loop was more uniform throughout the peel extension than for the control hook strip, which suggests an increased reliability of the fastener components, even when using hook strips having more than one or two rows of hook elements between the interrupted slits.

TABLE 2

| Specimen | Hook Strip | Delta Energy (mJ) | Max Load (gf) | Avg. Load (gf) | Avg. Peak (gf) |
|---|---|---|---|---|---|
| C4 | Control | 132.6 | 709.1 | 376.4 | 429.5 |
| C5 | Control | 127.9 | 1176.6 | 373.3 | 551.8 |
| C6 | Control | 322.4 | 1916.0 | 868.1 | 1386.7 |
| 4 | Ex. 1 | 322.6 | 1922.2 | 943.0 | 1190.9 |
| 5 | Ex. 1 | 300.3 | 1868.1 | 803.9 | 1136.4 |
| 6 | Ex. 1 | 359.2 | 2017.3 | 981.1 | 1453.1 |
| 7 | Ex. 2 | 103.5 | 699.3 | 277.0 | 412.8 |
| 8 | Ex. 2 | 194.1 | 1556.8 | 519.6 | 1077.9 |
| 9 | Ex. 2 | 152.2 | 1235.2 | 449.5 | 720.6 |

Table 3 summarizes the 180 degree peel data obtained when evaluating the hook strips using Loop C (nonwoven bonded loop). The results obtained for Control Example Specimens C7-C9 were similar to those obtained when evaluating the control hook strips with the knit loop and the extrusion bonded loop materials as described above. The load at low extension is low (first half of the curve) and then increases towards the end of the hook patch (second half of the peel curve). The results obtained for invention Specimens 10-12 of Hook Strip 1 were similar to those obtained for Specimens 1-6 with the knit loop and the extrusion bonded loop materials as described above. The peel force was more consistent throughout the peel curve and was at a higher force level in comparison to the peel curves for the control hook strips.

TABLE 3

| Specimen | Hook Strip | Delta Energy (mJ) | Max Load (gf) | Avg. Load (gf) | Avg. Peak (gf) |
|---|---|---|---|---|---|
| C7 | Control | 31.6 | 312.0 | 86.3 | 117.3 |
| C8 | Control | 36.0 | 279.0 | 104.0 | 145.3 |
| C9 | Control | 31.6 | 355.6 | 91.5 | 94.5 |
| 10 | Ex. 1 | 61.0 | 348.6 | 163.4 | 213.0 |
| 11 | Ex. 1 | 84.4 | 535.3 | 226.1 | 343.5 |
| 12 | Ex. 1 | 77.0 | 479.9 | 230.9 | 276.2 |

This disclosure may take on various modifications and alterations without departing from its spirit and scope. Accordingly, this disclosure is not limited to the above-described embodiments but is to be controlled by the limitations set forth in the following claims and any equivalents thereof. This disclosure may be suitably practiced in the absence of any element not specifically disclosed herein. All patents and patent applications cited above are hereby incorporated by reference into this document in their entirety.

What is claimed is:

1. A hook strip comprising:
    a backing having a first surface and a length in a first direction and first and second side edges;
    multiple rows of hook elements aligned in the first direction and projecting from the first surface of the backing; and
    interrupted slits cut through the backing between at least three pairs of adjacent rows of the hook elements, wherein each of the interrupted slits extends in the first direction and is interrupted by at least one intact bridging region of the backing;
    wherein the number of rows of the hook elements between at least some of the interrupted slits increases from the second side edge to the first side edge.

2. The hook strip of claim 1, wherein the backing is not joined to a carrier.

3. The hook strip of claim 1, wherein a distance between interrupted slits is smaller at the second side edge than at the first side edge.

4. The hook strip of claim 1, wherein for any two adjacent interrupted slits, the bridging regions are staggered in a cross direction perpendicular to the first direction.

5. A fastening laminate comprising a carrier and the hook strip of claim 1, wherein the backing has a second surface opposite the first surface, and wherein the second surface of the backing is joined to a portion of the carrier.

6. An absorbent article having at least a front waist region, a rear waist region, and a longitudinal center line bisecting the front waist region and the rear waist region, wherein at least one of the front waist region or the rear waist region comprises the fastening laminate of claim 5, wherein the fastening laminate has a proximal end attached to the absorbent article and a distal end where peel is initiated, and wherein the second side edge of the backing is closer than the first side edge to the distal end of the fastening laminate; and wherein the first direction of the hook strip is aligned with the longitudinal center line.

7. A hook strip comprising:
    a backing having a first surface and a length in a first direction;
    multiple rows of hook elements aligned in the first direction and projecting from the first surface of the backing;
    an interrupted slit cut through the backing between at least one pair of adjacent rows of the hook elements, wherein the interrupted slit extends in the first direction and is interrupted by at least one intact bridging region of the backing; and
    a partial-depth cut in the first surface of the backing in the at least one intact bridging region, wherein the partial-depth cut is collinear with the interrupted slit but does not extend through the backing.

8. The hook strip of claim 7, wherein the backing is not joined to a carrier.

9. The hook strip of claim 7, wherein there are interrupted slits cut through the backing between at least three pairs of adjacent rows of the hook elements, and wherein the number of rows of hook elements between at least some of the interrupted slits varies.

10. A fastening laminate comprising a carrier and the hook strip of claim 7, wherein the backing has a second surface opposite the first surface, and wherein the second surface of the backing is joined to a portion of the carrier.

11. A hook strip comprising:
    a backing having a first surface, a thickness, a length in a first direction, and no slits through the backing;

multiple rows of hook elements aligned in the first direction and projecting from the first surface of the backing; and a partial slit cut into the first surface of the backing between at least one pair of adjacent rows of the hook elements, wherein the partial slit extends in the first direction and penetrates the thickness of the backing in a range from 40 to 90 percent.

12. The hook strip of claim 11, wherein the hook elements have loop-engaging overhangs, and wherein at least a portion of each loop-engaging overhang extends at a nonzero angle to the partial slit.

13. The hook strip of claim 11, wherein the partial slit is interrupted by at least one bridging region of the backing that is not slit.

14. The hook strip of claim 11, wherein there are partial slits cut through the backing between at least three pairs of adjacent rows of the hook elements, and the number of rows of hook elements between at least some of the partial slits varies.

15. A fastening laminate comprising:
a carrier;
a backing having a first surface, a second surface opposite the first surface, a thickness, a length in a first direction, first and second side edges, a top edge and a bottom edge, wherein the second surface of the backing is joined to a portion of the carrier;
multiple rows of hook elements aligned in the first direction and projecting from the first surface of the backing; and
slits cut into the backing between at least three pairs of adjacent rows of the hook elements, wherein each of the slits extends in the first direction and forms abutting portions of the backing on either side of the slit, and wherein the number of rows of hook elements between at least some of the slits increases from the second side edge to the first side edge;
wherein at least the portion of carrier to which the second face of the backing is joined has up to a ten percent elongation in a second direction perpendicular to the first direction.

16. The fastening laminate according to claim 15, wherein each of the slits is cut through the thickness of the backing and extends from the top edge to the bottom edge of the backing to form separate, abutting strips of the backing on the carrier.

17. The fastening laminate according to claim 15, wherein each of the slits is a partial slit cut into the first face of the backing that penetrates only partially through the thickness of the backing.

18. The fastening laminate according to claim 15, wherein each of the slits is an interrupted slit that is cut through the backing and interrupted by a bridging region of the backing, wherein the bridging region of the backing is collinear with the interrupted slit but is not cut or penetrates only a portion of the thickness of the backing.

19. An absorbent article having at least a front waist region, a rear waist region, and a longitudinal center line bisecting the front waist region and the rear waist region, wherein at least one of the front waist region or the rear waist region comprises the fastening laminate of claim 18, wherein the fastening laminate has a proximal end attached to the absorbent article and a distal end where peel is initiated, and wherein the second side edge of the backing is closer than the first side edge to the distal end of the fastening laminate; and wherein the first direction of the hook strip is aligned with the longitudinal center line.

* * * * *